(12) United States Patent
Kim

(10) Patent No.: US 12,215,184 B2
(45) Date of Patent: Feb. 4, 2025

(54) POLYOL OR POLYTHIOL COMPOUND, PREPARATION METHOD THEREFOR, TRANSPARENT POLYURETHANE-BASED RESIN PREPARED THEREFROM, AND OPTICAL BODY

(71) Applicants: KS LABORATORIES CO., LTD., Jeollanam-do (KR); Keun Sik Kim, Suncheon-si (KR)

(72) Inventor: Keun Sik Kim, Suncheon-si (KR)

(*) Notice: Subject to any disclaimer, the term of this patent is extended or adjusted under 35 U.S.C. 154(b) by 0 days.

(21) Appl. No.: 18/481,995

(22) Filed: Oct. 5, 2023

(65) Prior Publication Data

US 2024/0052089 A1 Feb. 15, 2024

Related U.S. Application Data

(62) Division of application No. 16/486,475, filed as application No. PCT/KR2018/001884 on Feb. 13, 2018, now abandoned.

(30) Foreign Application Priority Data

Feb. 15, 2017 (KR) .................. 10-2017-0020263

(51) Int. Cl.

| | | |
|---|---|---|
| *C08G 18/72* | (2006.01) | |
| *C07C 319/08* | (2006.01) | |
| *C07C 321/04* | (2006.01) | |
| *C07C 321/14* | (2006.01) | |
| *C07C 323/12* | (2006.01) | |
| *C08G 18/24* | (2006.01) | |
| *C08G 18/38* | (2006.01) | |
| *C08G 18/73* | (2006.01) | |
| *C08G 18/75* | (2006.01) | |
| *C08G 18/78* | (2006.01) | |
| *C08L 75/04* | (2006.01) | |
| *G02B 1/04* | (2006.01) | |
| *G02C 7/02* | (2006.01) | |

(52) U.S. Cl.
CPC ............ *C08G 18/72* (2013.01); *C07C 319/08* (2013.01); *C07C 321/04* (2013.01); *C07C 321/14* (2013.01); *C07C 323/12* (2013.01); *C08G 18/24* (2013.01); *C08G 18/242* (2013.01); *C08G 18/38* (2013.01); *C08G 18/3876* (2013.01); *C08G 18/73* (2013.01); *C08G 18/755* (2013.01); *C08G 18/757* (2013.01); *C08G 18/758* (2013.01); *C08G 18/7831* (2013.01); *C08L 75/04* (2013.01); *G02B 1/04* (2013.01); *G02B 1/041* (2013.01); *G02C 7/02* (2013.01)

(58) Field of Classification Search
CPC ........ C08G 18/72; C08G 18/38; C08G 18/24; C08G 18/242; C08G 18/3876; C08G 18/73; C08G 18/757; C08G 18/758; C08G 18/7831; C07C 319/08; C07C 321/04; C07C 323/12; C07C 321/14; C08L 75/04; G02B 1/04; G02B 1/041; G02C 1/02; G02C 7/02
See application file for complete search history.

(56) References Cited

U.S. PATENT DOCUMENTS

| | | | |
|---|---|---|---|
| 3,824,259 A | 7/1974 | Oswald et al. | |
| 4,609,762 A | 9/1986 | Morris et al. | |

FOREIGN PATENT DOCUMENTS

| | | |
|---|---|---|
| CN | 1129811 A | 8/1996 |
| CN | 1215737 A | 5/1999 |
| EP | 0243546 A1 | 11/1987 |
| JP | S62273946 | 11/1987 |
| JP | H05208950 A | 8/1993 |
| JP | H07207195 A | 8/1995 |
| KR | 100180926 81 | 5/1999 |
| KR | 20110021371 | 3/2011 |
| KR | 20140134050 A | 11/2014 |
| KR | 20140141723 A | 12/2014 |
| KR | 20170078139 A | 7/2017 |
| WO | WO2007129449 A1 | 11/2007 |
| WO | WO2007129450 A1 | 11/2007 |
| WO | WO2014027665 A1 | 2/2014 |

OTHER PUBLICATIONS

International Search Report dated Jun. 15, 2018 for PCT/KR2018/001884.
Chemical Abstract Compound, STN express. RNs: 1848891-70-2 (Jan. 19, 2016), 1841160-61-9 (Jan. 5, 2016, 1690303-37-7 (Apr. 23, 2015, 1690271-90-9 (Apr. 23, 2015), 1566308-05-4 (Mar. 11, 2014), 1520646-10-9 (Jan. 15, 2014), 1880875-80-8 (Mar. 7, 2016), 1699070-45-5 (Mar. 6, 2015).
Registry(STN); CAS, A Devision of American Chemical Society; retrieved Mar. 4, 2022; pp. 1-16; www.cas.org/solutions/cas-scifinder-discovery/cas-scifinder.
E.V. Vasilyeva et al. "Comparative Evaluation of Stability of Dithiol Compounds With Bismuth and Copper Cations," Ukrainskii Khimicheskii Zhurnal, 1966, pp. 194-201, vol. 32(2).
Notice of Allowance dated Apr. 15, 2022 for Korean Application No. 10-2021-0121064.

*Primary Examiner* — Rabon A Sergent

(57) ABSTRACT

The present invention relates to a novel polyol or polythiol having three or more functional groups, a preparation method there for, and an optical body manufactured therefrom. Especially, the present invention relates to a poly(thio)urethane-based resin and an optical body, such as lenses, manufactured using the resin, wherein the poly(thio)urethane-based resin is prepared by obtaining a novel polyol and then combining a polythiol, which is prepared from the obtained polyol, with a polyiso(thio)cyanate.

6 Claims, 6 Drawing Sheets

POLYOL OR POLYTHIOL COMPOUND, PREPARATION METHOD THEREFOR, TRANSPARENT POLYURETHANE-BASED RESIN PREPARED THEREFROM, AND OPTICAL BODY

TECHNICAL FIELD

The present invention relates to a novel polyolorpolythiol, a method of preparing the same, and a polyurethane resin prepared therefrom. In particular, the present invention relates to an optical bodyformed of a poly(thio)urethane resin prepared by reacting a novel polythiol with a polyiso(thio)cyanate compound.

CROSS-REFERENCE TO RELATED APPLICATION

This application is a divisional application of the currently pending U.S. application Ser. No. 16/486,475 filed Aug. 15, 2019; which is a national stage application, filed under 35 U.S.C. § 371, of International Patent Application No. PCT/KR2018/001884, filed on Feb. 13, 2018; which claims the priority benefit to Korean Application No. 10-2017-0020263 filed Feb. 15, 2017; the entire contents of which are incorporated by reference herein in their entity.

BACKGROUND ART

In recent years, resins for plastic lenses are required to have further improved performance together with high refractivity, high Abbe's number, low specific gravity, high heat resistance, and the like. Currently, various resins for plastic lenses have been developed and used in the art. In particular, a poly(thio)urethane resin generally used for plastic lenses is recently applied to optical devices including eyeglass lenses, camera lenses, and the like.

The poly(thio)urethane resin is obtained by reacting a polythiol with a polyiso(thio)cyanate compound. The polythiol or a polyol as an intermediate compound thereof is broadly used for various applications as a raw material for optical bodies, poly(thio)urethane resins or synthetic resins, a crosslinking agent, an epoxy resin curing agent, a vulcanizing agent, a polymerization regulator, a metal complex, and a biochemical lubrication additive.

Although various functions may be provided to the poly(thio)urethane resin for lenses and optical bodies through modification of a polyiso(thio)cyanate compound used as a component of the poly(thio)urethane resin, there is a problem of limitation in kind thereof. Accordingly, the polythiol used as another component thereof may be modified to provide various functions to the poly(thio)urethane resin and there is a need for various polythiols.

A method of preparing such a polythiol is disclosed in various documents in the art, for example, Patent Documents 1 to 3. Patent Document 1 discloses a method of preparing a polythiol compound, in which the content of a certain additive present in 2-mercapto ethanol is restricted to within a predetermined range.

Patent Document 2 discloses a method in which the content of calcium present in thiourea is restricted to within a predetermined range. Patent Document 3 relates to a polythiol composition and use thereof, and discloses a polythiol compound having at least three mercapto groups and a polythiol composition comprising a small amount of a nitrogen-containing compound in which one mercapto group of the polythiol compound is substituted with a hydroxyl group. All of Patent Documents 1, 2 and 3 disclose the method of preparing a polythiol compound using 2-mercapto ethanol. In particular, Patent Document 2 discloses a general method for preparing a polythiol compound by reacting 2-mercapto ethanol with an epihalohydrin compound. Currently, the preparation of 2-mercaptoethanol restrictively starts from ethylene oxide.

On the other hand, Patent Document 4 was filed based on Korean Patent Application No. 10-2017-0020263 (Application Date: 2017 Feb. 15) and published on Jul. 7, 2017. This document discloses a polythiol compound prepared by preparing 1-mercapto-2-propanol from propylene oxide, followed by reacting with epichlorohydrin. However, the invention of this patent document has various problems in that preparation of a desired polythiol compound cannot be secured in an example disclosing that a polythiol intermediate compound was prepared from a polyol intermediate compound.

PRIOR LITERATURE

Patent Document (Patent Document 1) International Publication No. WO 2007/129449
(Patent Document 2) International Publication No. WO 2007/129450
(Patent Document 3) International Publication No. WO 2014/027665
(Patent Document 4) Korean Patent Laid-open Publication No. 10-2017-0078139

DISCLOSURE

Technical Problem

For a poly(thio)urethane resin reported in the related art, it is difficult to manufacture an optical lens satisfying dyeing properties while maintaining high heat resistance. The dyeing properties refer to physical properties of a transparent resin prepared through reaction of a polythiol with a polyiso(thio)cyanate compound. The dyeing properties of a certain resin are obtained by dyeing the resin for shielding visible light. In general, increase in heat resistance of a resin results in reduction in dyeing properties thereof and increase in dyeing properties of the resin results in reduction in heat resistance thereof. Therefore, there is a need for a polythiol capable of satisfying both high heat resistance and high dyeing properties of a transparent resin prepared from a poly(thio)urethane composition.

The inventors of the present invention have conducted various and intensive studies to develop a polythiol satisfying such requirements. As a result, it was found that heat resistance of a transparent resin can be improved by regulating the volume and size of side chains while maintaining the same structure in molecules among factors affecting the glass transition temperature (Tg) of the transparent resin. Based on this finding that heat resistance of the transparent resin can be improved while maintaining the dyeing properties thereof, the inventors invented a novel polythiol through modification of a molecular structure of a polythiol.

The present invention is aimed at providing a polyol or polythiol compound, which is prepared using a starting material instead of 2-mercapto ethanol used in the art and can secure high heat resistance of a transparent lens formed thereof while allowing easy coloration and good dyeing properties of the transparent lens, and a method of preparing the same. In addition, the present invention is aimed at providing an optical body formed of a poly(thio)urethane resin prepared by reacting a novel polythiol with apolyiso(thio)cyanate compound.

Technical Solution

One aspect of the present invention relates to a polyol or polythiol compound or an isomer thereof, the polyol or polythiol compound having at least three functional groups and represented by Formula (a) or (b):

$$HY\diagdown\underset{Ra}{\overset{}{\diagup}}\diagdown S-Rb \quad (a)$$

or $$HY\diagdown\diagup\underset{Ra}{\overset{}{\diagdown}}S-Rb \quad (b)$$

(where Y is an oxygen atom or a sulfur atom;
Ra is a lower alkyl group,
i) for the polyol, Rb is —CH₂CH(OH)CH₂F, —CH₂CH(OH)CH₂Cl, —CH₂CH(OH)CH₂Br, —CH₂CH(OH)CH₂I, —CH₂CH(OH)CH₂SCH₂CH(OH)CH₂SCH₂CH(OH)CH₃,
—CH₂CH(OH)CH₂SCH₂CH(OH)CH₂SCH(CH₃)CH₂OH,
—CH₂CH(OH)CH₂OH, —CH₂CH(OH)CH₂SCH₂CH(OH)CH₃, —CH₂CH(OH)CH₂SCH(CH₃)CH₂OH,
—CH₂CH(OH)CH₂SCH₂CH(OH)CH₂CH₃, —CH₂CH(OH)CH₂SCH(CH₂CH₃)CH₂OH, —CH₂CH(OH)CH₂SCH₂CH(OH)CH₂SCH₂CH(OH)CH₂CH₃, or
—CH₂CH(OH)CH₂SCH₂CH(OH)CH₂SCH(CH₂CH₃)CH₂OH;
ii) for the polythiol, Rb is —CH(CH₂SH)CH₂SH, —CH₂CH(CH₂SH)SH,
—CH₂CH(CH₂SH)SCH(CH₃)CH₂SH, —CH₂CH(CH₂SH)SCH₂CH(CH₃)SH,
—CH(CH₂SH)CH₂SCH(CH₃)CH₂SH, —CH(CH₂SH)CH₂SCH₂CH(CH₃)SH,
—CH₂CH(CH₂SH)SCH(CH₂CH₃)CH₂SH, —CH₂CH(CH₂SH)SCH₂CH(CH₂CH₃)SH,
—CH(CH₂SH)CH₂SCH(CH₂CH₃)CH₂SH, —CH(CH₂SH)CH₂SCH₂CH(CH₂CH₃)SH,
—CH(CH₂SH)CH₂SCH₂CH(CH₂SH)SCH(CH₃)CH₂SH,
—CH(CH₂SH)CH₂SCH₂CH(CH₂SH)SCH₂CH(CH₃)SH,
—CH(CH₂SH)CH₂SCH(CH₂SH)CH₂SCH(CH₃)CH₂SH,
—CH(CH₂SH)CH₂SCH(CH₂SH)CH₂SCH₂CH(CH₃)SH,
—CH₂CH(CH₂SH)SCH₂CH(CH₂SH)SCH(CH₃)CH₂SH,
—CH₂CH(CH₂SH)SCH₂CH(CH₂SH)SCH₂CH(CH₃)SH,
—CH₂CH(CH₂SH)SCH(CH₂SH)CH₂SCH(CH₃)CH₂SH,
—CH₂CH(CH₂SH)SCH(CH₂SH)CH₂SCH₂CH(CH₃)SH,
—CH(CH₂SH)CH₂SCH(CH₂SH)SCH(CH₂CH₃)CH₂SH,
—CH(CH₂SH)CH₂SCH₂CH(CH₂SH)SCH₂CH(CH₃)SH, —CH(CH₂SH)CH₂SCH₂CH(CH₂SH)SCH₂CH(CH₂CH₃)SH,
—CH(CH₂SH)CH₂SCH(CH₂SH)CH₂SCH(CH₂CH₃)CH₂SH,
—CH(CH₂SH)CH₂SCH(CH₂SH)CH₂SCH(CH₂CH₃)CH₂SH,
—CH₂CH(CH₂SH)SCH₂CH(CH₂SH)SCH(CH₂CH₃)CH₂SH,
—CH₂CH(CH₂SH)SCH₂CH(CH₂SH)SCH₂CH(CH₂CH₃)CH₂SH,
—CH₂CH(CH₂SH)SCH(CH₂SH)CH₂SCH(CH₂CH₃)CH₂SH, or
—CH₂CH(CH₂SH)SCH(CH₂SH)CH₂SCH₂CH(CH₂CH₃)SH).

In Formula (a) or (b), Y may be an oxygen atom; Ra may be a methyl or ethyl group, and Rb may be one substituent selected from the group consisting of the following substituents:
—CH₂CH(OH)CH₂F, —CH₂CH(OH)CH₂Cl, —CH₂CH(OH)CH₂Br, —CH₂CH(OH)CH₂I,
—CH₂CH(OH)CH₂SCH₂CH(OH)CH₂SCH₂CH(OH)CH₃,
—CH₂CH(OH)CH₂SCH₂CH(OH)CH₂SCH(CH₃)CH₂OH,
—CH₂CH(OH)CH₂OH,
—CH₂CH(OH)CH₂SCH₂CH(OH)CH₃,
—CH₂CH(OH)CH₂SCH(CH₃)CH₂OH,
—CH₂CH(OH)CH₂SCH₂CH(OH)CH₂CH₃,
—CH₂CH(OH)CH₂SCH(CH₂CH₃)CH₂OH,
—CH₂CH(OH)CH₂SCH₂CH(OH)CH₂SCH₂CH(OH)CH₂CH₃, and
—CH₂CH(OH)CH₂SCH₂CH(OH)CH₂SCH(CH₂CH₃)CH₂OH.

In addition, in Formula (a) or (b), Y may be a sulfur atom; Ra may be a methyl or ethyl group; and Rb may be one substituent selected from the group consisting of the following substituents:
—CH(CH₂SH)CH₂SH, —CH₂CH(CH₂SH)SH,
—CH₂CH(CH₂SH)SCH(CH₃)CH₂SH,
—CH₂CH(CH₂SH)SCH₂CH(CH₃)SH, —CH(CH₂SH)CH₂SCH(CH₃)CH₂SH, —CH(CH₂SH)CH₂SCH₂CH(CH₃)SH, —CH₂CH(CH₂SH)SCH(CH₂CH₃)CH₂SH, —CH₂CH(CH₂SH)SCH₂CH(CH₂CH₃)SH, —CH(CH₂SH)CH₂SCH(CH₂CH₃)CH₂SH, —CH(CH₂SH)CH₂SCH₂CH(CH₂CH₃)SH,
—CH(CH₂SH)CH₂SCH₂CH(CH₂SH)SCH(CH₃)CH₂SH,
—CH(CH₂SH)CH₂SCH₂CH(CH₂SH)SCH₂CH(CH₃)SH,
—CH(CH₂SH)CH₂SCH(CH₂SH)CH₂SCH(CH₃)CH₂SH,
—CH(CH₂SH)CH₂SCH(CH₂SH)CH₂SCH₂CH(CH₃)SH,
—CH₂CH(CH₂SH)SCH₂CH(CH₂SH)SCH(CH₃)CH₂SH,
—CH₂CH(CH₂SH)SCH₂CH(CH₂SH)SCH₂CH(CH₃)SH,
—CH₂CH(CH₂SH)SCH(CH₂SH)CH₂SCH(CH₃)CH₂SH,
—CH₂CH(CH₂SH)SCH(CH₂SH)CH₂SCH₂CH(CH₃)SH,
—CH(CH₂SH)CH₂SCH₂CH(CH₂SH)SCH(CH₂CH₃)CH₂SH,
—CH(CH₂SH)CH₂SCH₂CH(CH₂SH)SCH₂CH(CH₂CH₃)SH,
—CH(CH₂SH)CH₂SCH(CH₂SH)CH₂SCH(CH₂CH₃)CH₂SH, —CH(CH₂SH)CH₂SCH(CH₂SH)CH₂SCH₂CH(CH₂CH₃)SH,
—CH₂CH(CH₂SH)SCH₂CH(CH₂SH)SCH(CH₂CH₃)CH₂SH,
—CH₂CH(CH₂SH)SCH₂CH(CH₂SH)SCH₂CH(CH₂CH₃)SH,
—CH₂CH(CH₂SH)SCH(CH₂SH)CH₂SCH(CH₂CH₃)CH₂SH, and
—CH₂CH(CH₂SH)SCH(CH₂SH)CH₂SCH₂CH(CH₂CH₃)SH.

Another aspect of the present invention relates to a method of preparing a polythiol represented by Formula (1) or an isomer thereof according to Reaction Scheme 1, the method comprising the steps of:
(1) preparing an intermediate compound of Formula (5) by reacting a mercapto compound of Formula (2) with an epihalohydrin compound of Formula (4) in an equivalent ratio of 1:1;
(2) preparing a polyol compound of Formula (6) by adding an aqueous sodium sulfate solution to the prepared intermediate compound of Formula (5) and by reacting them; and
(3) adding an inorganic acid and thiourea to the prepared polyol compound of Formula (6), heating, stirring and cooling a mixture of the inorganic acid, thiourea and the polyol compound to room temperature, followed by adding a basic aqueous solution to a resulting product to hydrolyze the resulting product:

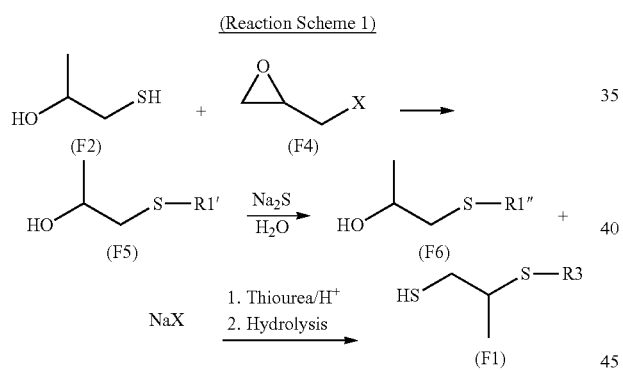

(Reaction Scheme 1)

(where
X is one selected from the group consisting of F, Cl, Br and I,
R1' is one selected from the group consisting of CH₂CH(OH)CH₂F, —CH₂CH(OH)CH₂Cl, —CH₂CH(OH)CH₂Br, and —CH₂CH(OH)CH₂I,
R1" is —CH₂CH(OH)CH₂SCH₂CH(OH)CH₂SCH₂CH(OH)CH₃ or —CH₂CH(OH)CH₂SCH₂CH(OH)CH₂SCH(CH₃)CH₂OH, and
R3 is one selected from the group consisting of
CH(CH₂SH)CH₂SCH₂CH(CH₂SH)SCH(CH₃)CH₂SH,
—CH(CH₂SH)CH₂SCH₂CH(CH₂SH)SCH₂CH(CH₃)SH,
—CH(CH₂SH)CH₂SCH(CH₂SH)CH₂SCH(CH₃)CH₂SH,
—CH(CH₂SH)CH₂SCH(CH₂SH)CH₂SCH₂CH(CH₃)SH,
—CH₂CH(CH₂SH)SCH₂CH(CH₂SH)SCH(CH₃)CH₂SH,
—CH₂CH(CH₂SH)SCH₂CH(CH₂SH)SCH₂CH(CH₃)SH,
—CH₂CH(CH₂SH)SCH(CH₂SH)CH₂SCH(CH₃)CH₂SH, and
—CH₂CH(CH₂SH)SCH(CH₂SH)CH₂SCH₂CH(CH₃)SH).

A further aspect of the present invention relates to a method of preparing a polythiol represented by Formula (1) or an isomer thereof according to Reaction Scheme 2, the method comprising the steps of:
(1) preparing an intermediate compound of Formula (7) by reacting 1 equivalent weight of a mercapto compound of Formula (3) with 1 equivalent weight of an epihalohydrin compound of Formula (4);
(2) preparing a polyol compound of Formula (8) by adding an aqueous sodium sulfate solution to the prepared intermediate compound of Formula (7) and by reacting them; and
(3) adding an inorganic acid and thiourea to the prepared polyol compound of Formula (8), heating, stirring and cooling a mixture of the inorganic acid, thiourea and the polyol compound to room temperature, followed by adding a basic aqueous solution to a resulting product to hydrolyze the resulting product:

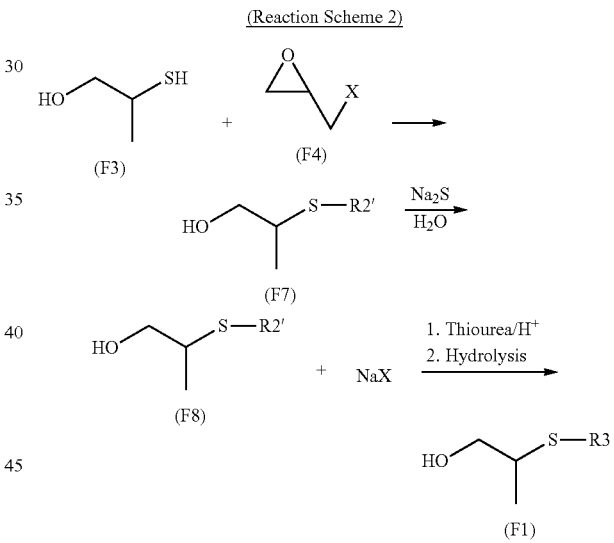

(Reaction Scheme 2)

(where
X is one selected from the group consisting of F, Cl, Br and I,
R2' is one selected from the group consisting of CH₂CH(OH)CH₂F, —CH₂CH(OH)CH₂Cl, —CH₂CH(OH)CH₂Br, and —CH₂CH(OH)CH₂I,
R2" is —CH₂CH(OH)CH₂SCH₂CH(OH)CH₂SCH₂CH(OH)CH₃ or —CH₂CH(OH)CH₂SCH₂CH(OH)CH₂SCH(CH₃)CH₂OH,
R3 is one selected from the group consisting of
—CH(CH₂SH)CH₂SCH₂CH(CH₂SH)SCH(CH₃)CH₂SH,
—CH(CH₂SH)CH₂SCH₂CH(CH₂SH)SCH₂CH(CH₃)SH,
—CH(CH₂SH)CH₂SCH(CH₂SH)CH₂SCH₂CH(CH₃)CH₂SH,
—CH(CH₂SH)CH₂SCH(CH₂SH)CH₂SCH₂CH(CH₃)SH, —CH$_2$CH(CH$_2$SH)SCH$_2$CH(CH$_2$SH)SCH(CH$_3$)CH$_2$SH,
—CH$_2$CH(CH$_2$SH)SCH$_2$CH(CH$_2$SH)SCH$_2$CH(CH$_3$)SH,
—CH$_2$CH(CH$_2$SH)SCH(CH$_2$SH)CH$_2$SCH(CH$_3$)CH$_2$SH, and
—CH$_2$CH(CH$_2$SH)SCH(CH$_2$SH)CH$_2$SCH$_2$CH(CH$_3$)SH).

Yet another aspect of the present invention relates to a method of preparing a polythiol represented by Formula (1) or an isomer thereof according to Reaction Scheme 3, the method comprising the steps of:
(1) preparing a polyol compound of Formula (5) or (7) by reacting a mercapto compound of Formula (2) or (3) with a glycidol compound in an equivalent ratio of 1:1; and
(2) adding an inorganic acid and thiourea to the prepared polyol compound of Formula (5) or (7), heating, stirring and cooling a mixture of the inorganic acid, thiourea and the polyol to room temperature, followed by adding a basic aqueous solution to a resulting product to hydrolyze the resulting product:

(Reaction Scheme 3)

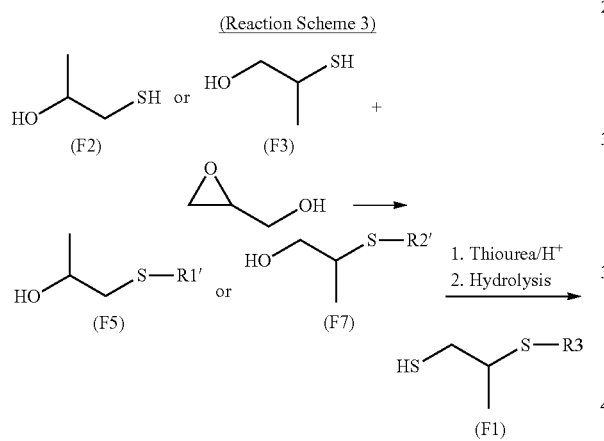

(where R1' and R2' are each CH$_2$CH(OH)CH$_2$OH and R3 is —CH(CH$_2$SH)CH$_2$SH or —CH$_2$CH(CH$_2$SH)SH).

Yet another aspect of the present invention relates to a method of preparing a polythiol represented by Formula (1) or an isomer thereof according to Reaction Scheme 4, the method comprising the steps of:
(1) preparing a polyol compound of Formula (5) or (7) by reacting a mercapto compound of Formula (2) or (3) with an epihalohydrin compound of Formula (4) in an equivalent ratio of 2:1; and
(2) adding an inorganic acid and thiourea to the prepared polyol compound of Formula (5) or (7), heating, stirring and cooling a mixture of the inorganic acid, thiourea and the polyol to room temperature, followed by adding a basic aqueous solution to a resulting product to hydrolyze the resulting product:

(Reaction Scheme 4)

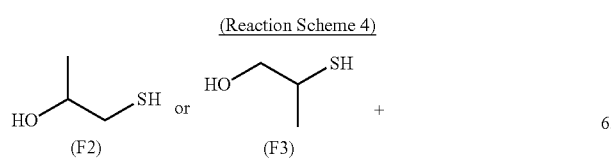

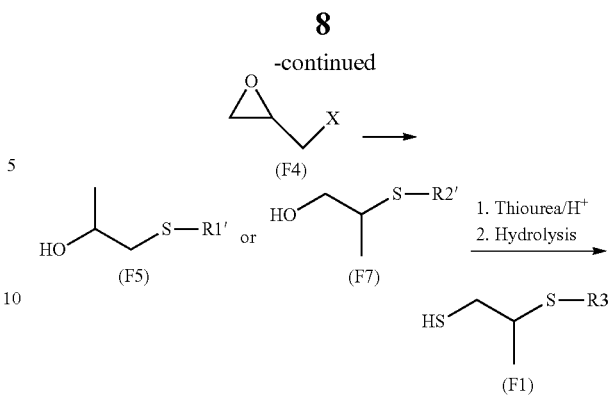

(where X is one selected from the group consisting of F, Cl, Br and I,
R1' and R2' are each CH$_2$CH(OH)CH$_2$SCH$_2$CH(OH)CH$_3$ or —CH$_2$CH(OH)CH$_2$SCH(CH$_3$)CH$_2$OH, and
R3 is —CH$_2$CH(CH$_2$SH)SCH$_2$CH(CH$_3$)SH, —CH$_2$CH(CH$_2$SH)SCH(CH$_3$)CH$_2$SH,
—CH(CH$_2$SH)CH$_2$SCH$_2$CH(CH$_3$)SH, or —CH(CH$_2$SH)CH$_2$SCH(CH$_3$)CH$_2$SH).

Yet another aspect of the present invention relates to a method of preparing a polythiol represented by Formula (11) according to Reaction Scheme 5, the method comprising the steps of:
(1) preparing an intermediate compound of Formula (15) by reacting a mercapto compound of Formula (12) with an epihalohydrin compound of Formula (4) in an equivalent ratio of 1:1;
(2) preparing a polyol compound of Formula (16) by adding an aqueous sodium sulfate solution to the prepared intermediate compound of Formula (15) and by reacting them; and
(3) adding an inorganic acid and thiourea to the prepared polyol compound of Formula (16), heating, stirring and cooling a mixture of the inorganic acid, thiourea and the polyol compound to room temperature, followed by adding a basic aqueous solution to a resulting product to hydrolyze the resulting product:

(Reaction Scheme 5)

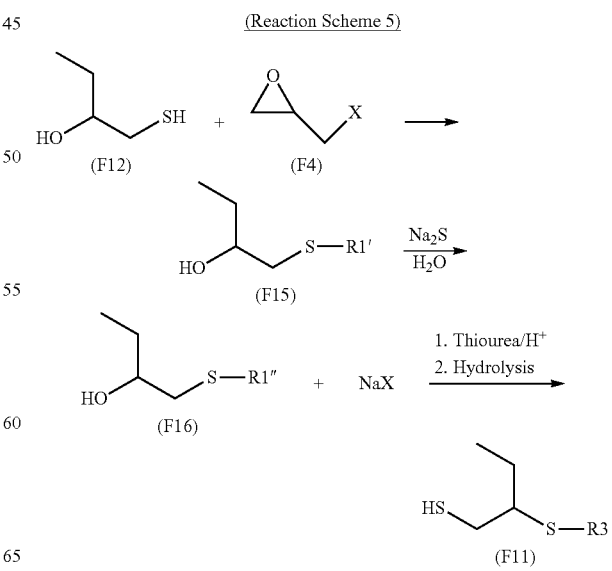

(where X and R1' are the same as each substituent of Reaction Scheme 1,

R1" is —CH$_2$CH(OH)CH$_2$SCH$_2$CH(OH)CH$_2$SCH$_2$CH(OH)CH$_2$CH$_3$,

R3 is one selected from the group consisting of —CH(CH$_2$SH)CH$_2$SCH$_2$CH(CH$_2$SH)SCH(CH$_2$CH$_3$)CH$_2$SH, —CH(CH$_2$SH)CH$_2$SCH$_2$CH(CH$_2$SH)SCH$_2$CH(CH$_2$CH$_3$)SH, —CH(CH$_2$SH)CH$_2$SCH(CH$_2$SH)CH$_2$SCH(CH$_2$CH$_3$)CH$_2$SH, —CH(CH$_2$SH)CH$_2$SCH(CH$_2$SH)CH$_2$SCH$_2$CH(CH$_2$CH$_3$)SH, —CH$_2$CH(CH$_2$SH)SCH(CH$_2$SH)SCH(CH$_2$CH$_3$)CH$_2$SH, —CH$_2$CH(CH$_2$SH)SCH$_2$CH(CH$_2$SH)SCH$_2$CH(CH$_2$CH$_3$)SH, —CH$_2$CH(CH$_2$SH)SCH(CH$_2$SH)CH$_2$SCH(CH$_2$CH$_3$)CH$_2$SH, and —CH$_2$CH(CH$_2$SH)SCH(CH$_2$SH)CH$_2$SCH$_2$CH(CH$_2$CH$_3$)SH).

Yet another aspect of the present invention relates to a method of preparing a polythiol represented by Formula (11) or an isomer thereof according to Reaction Scheme 6, the method comprising the steps of:

(1) preparing a polyol compound of Formula (15) by reacting a mercapto compound of Formula (12) with an epihalohydrin compound of Formula (4) in an equivalent ratio of 2:1; and (2) adding an inorganic acid and thiourea to the prepared polyol compound of Formula (15), heating, stirring and cooling a mixture of the inorganic acid, thiourea and the polyol to room temperature, followed by adding a basic aqueous solution to a resulting product to hydrolyze the resulting product:

(Reaction Scheme 6)

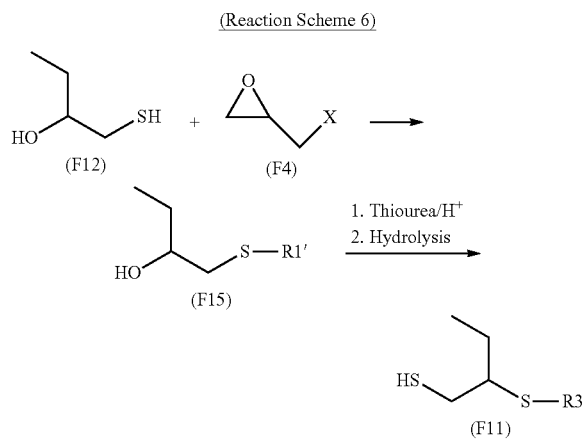

(where
X is one selected from the group consisting of F, Cl, Br and I,

R1' is CH$_2$CH(OH)CH$_2$SCH$_2$CH(OH)CH$_2$CH$_3$,

R3 is —CH$_2$CH(CH$_2$SH)SCH(CH$_2$CH$_3$)CH$_2$SH, —CH$_2$CH(CH$_2$SH)SCH$_2$CH(CH$_2$CH$_3$)SH, —CH(CH$_2$SH)CH$_2$SCH(CH$_2$CH$_3$)CH$_2$SH, or —CH(CH$_2$SH)CH$_2$SCH$_2$CH(CH$_2$CH$_3$)SH).

In the method of preparing the polythiol represented by Formula (1), TEA or NaOH may be used as a catalyst. Further, in the method of preparing the polythiol represented by Formula (1), the inorganic acid may be hydrochloric acid, nitric acid, sulfuric acid, or hydrobromic acid. Furthermore, the basic aqueous solution may bean aqueous ammonia solution, an aqueous sodium hydroxide solution, an aqueous lithium hydroxide solution, or hydrazine.

The alcohol intermediate compound of Formula (5), (7) or (15) is prepared by reacting, as a starting material, about 2 or more equivalent weights of a mercapto-ethyl alcohol substituted with a lower alkyl group, such as the compound of Formula (2) or (3) in Reaction Scheme 4 or the compound of Formula (12) in Reaction Scheme 6, with 1 equivalent weight of the epichlorohydrin compound of Formula (4), and has a symmetrical structure.

In addition, the halo-alcohol intermediate compound of Formula (5), (7) or (15) is prepared by reacting, as a starting material, about 1 equivalent weight of a mercaptoethyl alcohol substituted with a lower alkyl group, such as the compound of Formula (2) in Reaction Scheme 1, the compound of Formula (3) in Reaction Scheme 2, or the compound of Formula (12) in Reaction Scheme 5, with 1 equivalent weight of the epichlorohydrin compound of Formula (4).

The polyol intermediate compound of Formula (6), (8) or (16) is prepared by reacting about 1 equivalent weight of the compound of Formula (5) in Reaction Scheme 1, the compound of Formula (7) in Reaction Scheme 2, or the compound of Formula (15) in Reaction Scheme 5 with 0.5 equivalent weight of Na$_2$S, and has a symmetrical structure.

As mentioned in the background technique, in Preparation Example (1) and Comparative Example (1) of Patent Document 4 (KR Patent Laid-open Publication No. 10-2017-0078139), an epichlorohydrin or epoxy compound substituted with a halo-alkyl group is reacted with a mercaptoethyl alcohol or a mercaptoethyl alcohol substituted with a lower alkyl group. However, since a polyol intermediate compound prepared by this reaction has an asymmetrical structure, a polythiol cannot be prepared from such a polyol intermediate compound or through such an asymmetrical polyol intermediate compound, in light of Reaction Formulas 1 to 6.

Yet another aspect of the present invention relates to a polyol compound as an intermediate compound of the polythiol compound, which may be prepared by the method of preparing the polyol of Formula (6) or (8), which includes Steps (1) and (2), in Reaction Scheme 1 or 2. In addition, another polyol compound may be prepared by the method of preparing the polyol of Formula (7), which includes Step (1), in Reaction Scheme 3 or 4. As in the method of preparing a polythiol, the method of preparing the polyol compound as an intermediate compound may employ TEA or NaOH as a catalyst.

Yet another aspect of the present invention relates to a poly(thio)urethane resin composition comprising the polythiol having at least three functional groups, which is prepared by one of the methods described above, and a polyisocyanate. Here, a mole ratio (=NCO/SH) of a functional group (—NCO) of the polyisocyanate to a functional group (—SH) of the polythiolcompound ranges from 0.6 to 2.0, preferably from 0.8 to 1.3, more preferably from 0.9 to 1.1. Within this range, the poly(thio)urethane resin composition can secure balance between various functions including refractivity, heat resistance, and the like, which are required for an optical material and a transparent material for plastic lenses.

Yet another aspect of the present invention relates to a poly(thio)urethane resin formed by heating and curing the poly(thio)urethane resin composition. Furthermore, yet another aspect of the present invention relates to a poly(thio)urethane plastic optical body manufactured by a method of preparing a poly(thio)urethane plastic lens, which includes polymerizing the poly(thio)urethane resin composition in a mold and releasing a molded product from the mold. Here, a mole ratio (═NCO/SH) of a functional group (—NCO) of the polyisocyanate to a functional group (—SH) of the polythiol compound ranges from 0.6 to 2.0, preferably from 0.8 to 1.3, more preferably from 0.9 to 1.1.

Although the plastic optical body of the present invention may be applied not only to an optical lens, but also to large-area windows, such as sliding windows, single or double hung windows, side-hinged windows, and the like, which are used in buildings and the like, a plastic optical lens will be mainly described as one example of the plastic optical body in the following description.

BEST MODE

Figure 1:
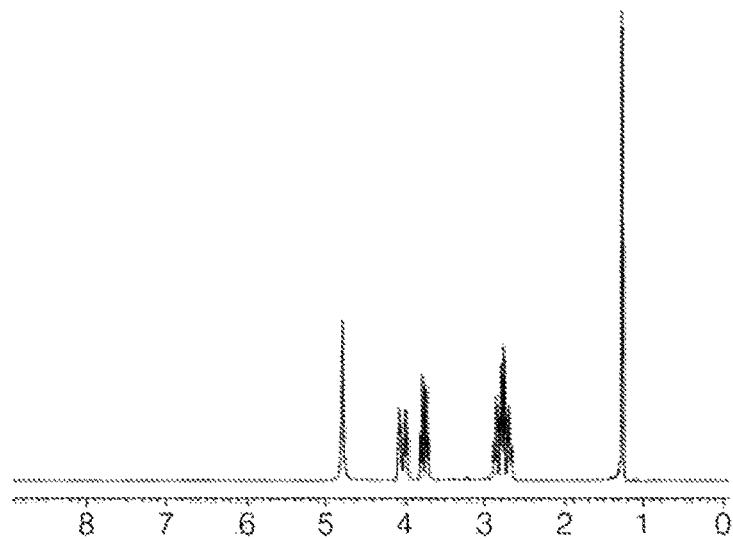
FIG. 1 shows $^1$H-NMR spectrum of Example 1 (Compound 1) according to the present invention.

Hereinafter, embodiments of the present invention will be described in detail with reference to the accompanying drawings.

Among mechanical properties of a lens produced from a polyurethane resin, heat resistance of the lens is related to the glass transition temperature Tg of the polyurethane resin, which has a correlation with dyeing properties thereof related to color uniformity. Accordingly, increase in glass transition temperature Tg tends to deteriorate the dyeing properties. In general, a chemical structure affecting a glass transition temperature Tg of a polymer compound may be examined from the point of view of flexibility of a main chain and flexibility of a side chain. In comparison of flexibility of main chains, a main chain having a benzene ring therein has lower flexibility of a main chain having no benzene ring and increases the glass transition temperature Tg. In comparison of flexibility of side chains, a side chain having a bulk functional group causing steric hindrance has low flexibility due to deterioration in rotatability, thereby causing increase in glass transition temperature Tg. Polyethylene and polypropylene may be recited by way of example. As a result, it can be confirmed that a polymer containing polypropylene glycol has a higher glass transition temperature Tg than a polymer containing polyethylene glycol.

Based on this fact, the inventors of the present invention attempted to synthesize a novel polythiol using propylene oxide or butylene oxide as a starting material for preparation of 2-mercapto ethanol, instead of ethylene oxide used in the art. In this case, a unit molecule from ethylene oxide (C-2) to propylene oxide (C-3), butylene oxide (C-4), and the like was changed while maintaining the same structure sequence in the molecule. Then, it was anticipated that, when the number of hydrogen atoms of an ethyl group increases due to a methyl molecule, the glass transition temperature Tg would increase due to influence of side chains, thereby completing the present invention.

According to the present invention, a polyol or polythiol compound having at least three functional groups and represented by Formula (a) or (b) may be prepared by a process according to Reaction Formulas 1 to 6.

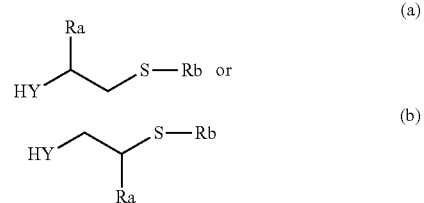

Herein, unless specifically stated otherwise, a 'halogen' represented by 'X' refers to fluorine, chlorine, bromine, or iodine, preferably chlorine.

Herein, a 'lower alkyl group' refers to a linear or branched alkyl group having 1 to 8 carbon atoms, preferably 1 to 6 carbon atoms, more preferably 1 to 4 carbon atoms. Specifically, the lower alkyl group may be a methyl group, an ethyl group, an n-propyl group, an n-butyl group, an n-pentyl group, an n-hexyl group, an n-heptyl group, an n-octyl group, an isopropyl group, an isobutyl group, a sec-butyl group, a tert-butyl group, an isopentyl group, or the like, preferably a methyl group or an ethyl group.

Polyol Compounds 1 to 9 represented by Formula (a) or (b) where Y is an oxygen atom, Ra is a methyl group or an ethyl group, and Rb is one substituent selected from the group consisting of the afore mentioned substituents may have the following structures and are named as follows.

| Compound No. | Structural Formula | Compound Name |
|---|---|---|
| 1 | HO−⟨⟩−S−⟨⟩(OH)−Cl | 1-chloro-3-((2-hydroxypropyl)thio)propane-2-ol |

-continued

| Compound No. | Structural Formula | Compound Name |
|---|---|---|
| 2 | HO-CH(CH3)-CH2-S-CH2-CH(OH)-CH2-Cl | 2-((3-chloro-2-hydroxypropyl)thio)-propane-1-ol |
| 3 | HO-CH(CH3)-CH2-S-CH2-CH(OH)-CH2-OH | 3-((2-hydroxypropyl)thio)propane-1,2-diol |
| 4 | HO-CH(CH3)-CH2-S-CH2-CH(OH)-CH2-S-CH2-CH(CH3)-OH | 1,3-bis[2-hydroxypropyl)thio]propane-2-ol |
| 5 | HO-CH(CH3)-CH2-S-CH2-CH(OH)-CH2-S-CH2-CH(OH)-CH2-S-CH2-CH(CH3)-OH | bis[3-((2-hydroxypropyl)thio)-2-hydroxypropyl]sulfide |
| 6 | HO-CH2-CH(CH3)-S-CH2-CH(OH)-CH2-S-CH2-CH(OH)-CH2-S-CH(CH3)-CH2-OH | bis[3-((1-hydroxy-propane-2-yl)thio)-2-hydroxypropyl]sulfide |
| 7 | CH3-CH2-CH(OH)-CH2-S-CH2-CH(OH)-CH2-Cl | 1-((3-chloro-2-hydroxypropyl)thio)butane-2-ol |
| 8 | CH3-CH2-CH(OH)-CH2-S-CH2-CH(OH)-CH2-S-CH2-CH(OH)-CH2-S-CH2-CH(OH)-CH2-CH3 | bis[3-((2-hydroxybutyl)thio)-2-hydroxypropyl]sulfide |
| 9 | CH3-CH2-CH(OH)-CH2-S-CH2-CH(OH)-CH2-S-CH2-CH(OH)-CH2-CH3 | 1,3-bis[2-hydroxybutyl)thio]propane-2-ol |

Further, among compounds represented by Formula (a) or (b) where Y is a sulfur atom, Ra is a methyl group or an ethyl group, and Rb is one selected from the group consisting of the aforementioned substituents, Polythiol Compounds 10 to 14 having the following structures and each having isomers as follows are obtained.

In preparation of the polythiol compounds, it could be confirmed that an intermediate compound could be produced through rearrangement resulting from steric hindrance upon preparation of a sulfide intermediate compound through reaction of each of the polyol intermediate compounds mentioned above with the thiourea/hydrochloric acid. Upon hydrolysis of the intermediate compound, a primary polythiol may be obtained as a resulting compound. As a result of structural analysis of a polythiol to be prepared by the method according to the present invention, it could be confirmed that the primary thiol compound is produced as a main product together with a secondary polythiol. As a result, it can be confirmed that a polythiol composition to be prepared by the method according to the present invention consists of a mixture of isomers. The following table shows theoretically producible isomers.

(1) Isomers of Compound 10 (GPT) and Compound 11 (MPT)

| Compound No. | Structural Formula | Compound Name | Acronym |
|---|---|---|---|
| 10-1 | HS-CH2-CH(CH3)-S-CH(CH2SH)-CH2-SH | 2-((1-mercaptopropan-2-yl)thio)propane-1,3-dithiol | GPT |

-continued

| Compound No. | Structural Formula | Compound Name | Acronym |
|---|---|---|---|
| 10-2 | | 2-((2-mercaptopropyl)thio)propane-1,3-dithiol | |
| 10-3 | | 3-((2-mercaptopropyl)thio)propane-1,2-dithiol | |
| 10-4 | | 3-((1-mercaptopropan-2-yl)thio)propane-1,2-dithiol | |
| 11-1 | | 3-((1-mercaptopropan-2-yl)thio)-2-((1-mercaptopropan-2-yl)thio)propane-1-thiol | MPT |
| 11-2 | | 3-((1-mercaptopropan-2-yl)thio)-2-((2-mercaptopropyl)thio)propane-1-thiol | |
| 11-3 | | 2-((1-mercaptopropan-2-yl)thio)-3-((2-mercaptopropyl)thio)propane-1-thiol | |
| 11-4 | | 2-((2-mercaptopropyl)thio)-3-((2-mercaptopropyl)thio)propane-1-thiol | |

(2) Isomers of Compound 12 (BPT)

| Compound No. | Structural Formula |
|---|---|
| 12-1 | |
| 12-2 | |
| 12-3 | |
| 12-4 | |

| Compound No. | Structural Formula |
|---|---|
| 12-5 | |
| 12-6 | |
| 12-7 | |
| 12-8 | |
| 12-9 | |
| 12-10 | |

General names of representative Compounds 12-1 to 12-3 are as follows and names of other compounds are omitted:

Compound 12-1: 3,3'-thiobis(2-(1-mercaptopropan-2-yl)thio)-1-propanethiol;

Compound 12-2: 2-((3-mercapto-2-((1-mercaptopropan-2-yl)thio)propyl)thio)-3-((1-mercaptopropan-2-yl)thio)propane-1-thiol; and Compound 12-3: 2,2'-thiobis(3-(1-mercaptopropan-2-yl)thio)-1-propanethiol (3) Isomers of Compound 13 (BBT) and Compound 14 (MBT)

Although Compound 13 (BBT) may have 10 isomers, Compounds 13-1, 13-2 and 13-3 are illustrated as representative isomers thereof, and although Compound 14 (MBT) may have four isomers, Compounds 14-1 and 14-2 are illustrated as representative isomers thereof.

| Compound No. | Structural Formula | Compound Name | Acronym |
|---|---|---|---|
| 13-1 | | 2,2'-((thiobis(1-mercaptopropane-3,2-diyl))bis(sulfanediyl)bis(butane-1-thiol) | BBT |
| 13-2 | | 2,2'-((thiobis(3-mercaptopropane-2,1-diyl))bis(sulfanediyl)bis(butane-1-thiol) | |

-continued

| Compound No. | Structural Formula | Compound Name | Acronym |
|---|---|---|---|
| 13-3 | HS, SH, HS, SH (structure) | 2-((3-mercapto-2-((3-mercapto-2-((1-mercaptobutan-2-yl)thio)propyl)thio)propyl)thio)butane-1-thiol | |
| 14-1 | (structure) | 3-((1-mercaptobutan-2-yl)thio)-2-((1-mercaptobutan-2-yl)thio)propane-1-thiol | MBT |
| 14-2 | (structure) | 2-((2-mercaptobutyl)thio)-3-((2-mercaptobutyl)thio)propane-1-thiol | |

Next, a method of preparing Polyol Compounds 1 to 9 will be described and a method of preparing Polythiol Compounds 10 to 16 from the prepared polyol compounds will be described.

(Polyol Preparation Method)

As shown in Reaction Formulas 1 to 6, the polyol compound according to the present invention may be prepared by reacting an epihalohydrin compound or a glycidol compound with a mercapto compound as an intermediate compound of a polythiolin an equivalent ratio of 1:1 or in an equivalent ratio of 2:1, as described above.

The epihalohydrin compound may be represented by Formula 4 (where X is a halogen atom) and may be obtained from commercially available products:

(Formula 4)

In addition, the glycidol compound (glycide; hydroxymethyl ethylene oxide) may be represented by the following formula and may be obtained from commercially available products:

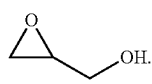

Obviously, such a glycidol compound may be prepared by reacting benzoyl peroxide with allyl alcohol or by heating epichlorohydrin together with potassium acetic anhydride to prepare acetate and treating the prepared acetate with sodium hydroxide in ether by a method known in the art.

Synthesis reaction of the polyol may be performed at a temperature of 10° C. to 50° C., preferably 20° C. to 30° C. If the reaction is performed at a lower temperature than 10° C., low reaction conversion can occur due to decrease in reaction rate. If the reaction is performed at a higher temperature than 50° C., the compound of Formula (2), (3) or (12) reacting with epichlorohydrin in the Reaction Formulas can be produced together with an impurity or a dimer. In addition, the compound of Formula (2), (3) or (12) used as a starting material of the mercapto compound may be added for 0.5 to 10 hours, preferably 1 to 2 hours. If the starting material is added for less than 0.5 hours, control of the reaction rate can be difficult and the compound of Formula (2), (3) or (12) can be produced together with an impurity or a dimer. The reaction temperature and the reaction time may be suitably regulated within the above ranges depending upon properties of each reactant and a solvent to be used.

For Compounds 1, 2, 3 and 7, each of the compounds of Formulas (2), (3) and (12) may be used in an amount of 1 mole, preferably 0.9 moles to 1.1 moles, with respect to 1 mole of epihalohydrin. If the compound is used in an amount of less than 0.9, unreacted epihalohydrincan remain as an impurity affecting subsequent reaction. If the compound is used in an amount of greater than 1.1 mole, unreacted 2-mercaptopropanol reacts with a reaction product to produce an impurity having a symmetrical structure wherein 2-mercaptopropanol is coupled to both sides of epihalohydrin. However, for Compounds 4 and 9, each of the compounds of Formulas (2), (3) and (12) may be used in an amount of 2 moles, preferably 2 moles to 3 moles, with respect to 1 mole of epihalohydrin. If the compound is used in an amount of less than 2 moles, an impurity having an asymmetrical structure can be produced through reaction of 1 mole of 2-mercaptopropanol and 1 mole of epihalohydrin and can affect subsequent reaction. If the compound is used in an amount of greater than 3 moles, an unreacted compound of Formula (2), (3) and (12) can remain and affects the subsequent reaction. Although Compounds 5, 6, and 8 may be prepared by the above method, each of the compounds of Formulas (2), (3) and (12) may be used in a similar equivalent weight in order to suppress generation of an impurity.

(Polythiol Preparation Method)

A sodium halogenide is additionally added to the prepared polyol compound and an inorganic acid and thiourea are added to the mixture, followed by heating, stirring and cooling the mixture to room temperature. Then, a basic aqueous solution is applied to the mixture to produce a polythiol compound through hydrolysis of the mixture. The prepared polythiol compound may be subjected to a work-up process such as solvent removal, filtration, vaporization, purification, and the like.

As used herein, the inorganic acid may be selected from among hydrochloric acid, nitric acid, sulfuric acid, hydrobromic acid, and the like. When used as the inorganic acid, hydrobromic acid may be used in an amount of 3 to 5 moles with respect to 1 mole of the polyol compound. Here, reaction may be performed at a temperature of 100° C. to 105° C. If the reaction is performed at a temperature of less than 100° C., the reaction rate can significantly decrease. The reaction may be performed for 3 hours to 8 hours and a reaction finish time may be confirmed based on whether the polyol compound is completely consumed. As the inorganic acid, the hydrochloric acid may be used in an amount of 3 to 5 moles with respect to 1 mole of the polyol compound. Here, reaction may be performed at a temperature of 105° C. to 110° C. The reaction may be performed for 12 hours to 24 hours and a reaction finish time may be confirmed based on whether the polyol compound is completely consumed.

As used for hydrolysis, the basic aqueous solution may be selected from among an aqueous ammonia solution, an aqueous sodium hydroxide solution, an aqueous lithium hydroxide solution, and hydrazine, preferably an aqueous ammonia solution. Although sodium hydroxide and lithium hydroxide can cause precipitation of an impurity having low solubility and deterioration in yield, sodium hydroxide and lithium hydroxide do not affect purity. The basic aqueous solution may be used in an amount of 3 moles to 10 moles with respect to 1 mole of the polyol compound. Here, reaction may be performed at a temperature of 20° C. to 100° C., preferably 40° C. to 70° C. Although reaction can occur without a solvent, the solvent may be selected from among toluene, methylene chloride, xylene, chlorobenzene, and dichlorobenzene, preferably toluene.

Generally, a polyurethane-based eyeglass lens is produced by heat-curing a uniform optical composition in a glass mold, followed by releasing a molded product from the glass mold, in which the uniform optical composition is prepared by mixing polyisocyanateas a polyurethane compound having a liquid phase (I) with a polyol or polythiol compound having a liquid phase (II), followed by degassing.

As the compound having a liquid phase (I), the polyiso (thio)cyanate compound may be selected from any compounds having at least one iso(thio)cyanate group without being limited to a particular compound. Examples of the polyiso(thio)cyanate compound may be classified into an aliphatic polyisocyanate, an alicyclic polyisocyanate, and an aromatic polyisocyanate, and specific examples thereof are disclosed in prior documents and thus are not specifically recited herein.

Among these polyisocyanate compounds, m-xylylene diisocyanate (XDI), 2,5 (6)-bis(isocyanate methyl)-bicyclo[2, 2,1]heptane (NBDI), 1,6-hexamethylenediisocyanate (HDI), isophoronediisocyanate (IPDI), and dicyclohexylmethanediisocyanate (HMDI) are preferably used, and biuret derivatives of isocyanate and trimer derivatives (for example, polyisocyanurate) of isocyanate may also be used.

The biuret type isocyanate may be easily prepared using 1,2-ethylene diisocyanate, 1,3-propylene diisocyanate, 1,4-butylene diisocyanate, 1,6-hexamethylene diisocyanate, 1,7-heptamethylene diisocyanate, 1,8-octamethylene diisocyanate, 1,9-nonamethylene diisocyanate, or 1,10-decamethylene diisocyanate as a raw material. In addition, the prepared biuret type isocyanate may be used after purification or as a mixture of raw monomer materials. Alternatively, the biuret type isocyanate may be obtained from commercially available products such as Desmodur N100 (Bayer Co., Ltd.) or Tolonate HDB LV (Perstop Co., Ltd.). In addition, the trimer type isocyanate may be easily prepared using the same raw materials as the raw materials for the biuret type isocyanate or may be obtained from commercially available products, such as Tolonate HDT LV (Vencorex Co., Ltd.), and the like.

In addition, as the compound having a liquid phase (II), the polythiol may further include additional polythiol compounds as well as the polythiol compound prepared by the method according to the present invention. The additional polythiol compound may be selected from any compounds having at least one thiol group or mixtures thereof, without limitation. Particularly, the polythiol compound may include at least one selected from the group consisting of 1,2-bis(2-mercaptoethylthio)-3-mercaptopropane, trimethylolpropanetris(mercaptopropionate), pentaerythritoltetrakis(mercaptopropionate), 2,3-bis(2-mercaptoethylthio) propane-1-thiol, 2-(2-mercaptoethylthio)-3-[2-(3-mercapto-2-(2-mercaptoethylthio)-propylthio]ethylthio-propane-1-thiol, 2-(2-mercaptoethylthio)-3-{2-mercapto-3-[3-mercapto-2-(2-mercaptoethylthio)-propylthio] propylthio}-propane-1-thiol, trimethylolpropanetris (mercaptopropionate, trimethylolethanetris (mercaptopropionate), glyceroltris(mercaptopropionate), trimethylolchlorotris(mercaptopropionate), trimethylolpropanetris(merc aptoacetate), trimethylolethanetris(mercaptoacetate), pentaerythritoltetrakis(mercaptopropionate), pentaerythritoltetrakis(mercaptoacetate), [1,4] dithiane-2-yl-methanethiol, 2-(2-mercaptoethylsulfanyl)-propane-1,3-dithiol, 2-([1,4]dithiane-2-ylmethylsulfanyl)-ethanethiol, 3-(3-mercaptopropionylsulfanyl)-propionic acid 2-hydroxylmethyl-3-(3-mercapto-propionyloxy)-2-(3-mercapto-propionyloxymethyl)-propylester, 3-(3-mercaptopropionylsulfanyl)-propionic acid 3-(3-mercaptopropionyloxy)-2,2-bis-(3-mercapto-propionyloxymethyl)-propylester, (5-mercaptomethyl-[1, 4]dithiane-2-yl)-methanethiol, 1,3-bis(2-mercaptoethylthio)propane-2-thiol (GST), (3,6,10,13-tetrathiapentadecane-1,8,15-trithiol)(SET), 2-(2-mercaptoethylthio)propane-1,3-dithiol (GMT), 4,8-dimercaptomethyl-1,11-dimercapto-3,6,9-trithiaundecane (DMDDU), and mixtures thereof.

Among these polythiol compounds, 1,3-bis(2-mercaptoethylthio)propane-2-thiol (GST), (3,6,10,13-tetrathiapentadecane-1,8,15-trithiol)(SET), and pentaerythritoltetrakis (mercaptopropionate) (PEMP) are preferably used. More preferably, a mixture of 1,3-bis(2-mercaptoethylthio)propane-2-thiol (GST) and pentaerythritoltetrakis(mercaptopropionate) (PEMP) is used.

A mole ratio (NCO/SH) of a functional group (—NCO) of the polyisocyanate used as the compound having a liquid phase (I) to a functional group (—SH) of the polythiol used as the compound having a liquid phase (II) may be in the range of 0.5 to 1.5. Preferably, the mole ratio ranges from 0.9 to 1.1, more preferably, 1.0, to secure further improved properties of the optical lens.

When HDI biuret, HDI trimer (HDI derivative), HDI, and IPDI are used together as the polyisocyanate, these compounds may be used in a weight ratio of 30 to 40:20 to 30:30 to 40. Although the polythiol prepared by the method according to the present invention may be used alone, typical polythiols, such as GST, PEMP, and the like, may be suitably mixed therewith in order to achieve desired refractivity and impact resistance, as needed.

In preparation of the polymerizable composition according to the present invention, the composition may include various additives in order to obtain essential optical properties for lenses, such as transparency, refractivity, specific gravity, impact resistance, heat resistance, and viscosity of a resin prepared from the polymerizable composition, as needed. The composition may further include a UV or near-IR absorbent, dyes, a light stabilizer, an antioxidant, and the like, as additives. Furthermore, the composition may further include an epoxy compound copolymerizable with a urethane resin composition, a thio-epoxy compound, a vinyl group or unsaturated group-containing compound, or a metal compound.

Further, in order to regulate the reaction rate, the composition may further include a catalyst. The catalyst may be, for example, a catalyst for urethane reaction and may be selected from tincompounds, such as dibutyltindilaurate, dibutyltin dichloride, dimethyltin dichloride, tetramethyl diacetoxydistannoxane, tetraethyl diacetoxydistannoxane, tetrapropyl diacetoxy distannoxane, and tetrabutyl diacetoxy distannoxane, or amine compounds including tertiary amine. These may be used alone or as a mixture thereof. The catalyst may be present in an amount of 0.001 wt % to 1wt % based on the total weight of monomers of the composition. Within this range, the composition can have good properties in terms of polymerizability, pot life, transparency, various optical properties or light resistance of a resin produced therefrom.

In addition, the resin composition for optical lenses according to the present invention may further include a bluing agent for correction of an initial color of a lens. Examples of the bluing agent may include an organic dye, an organic pigment, an inorganic pigment, and the like. Such an organic dye may be present in an amount of 0.1 to 50,000 ppm, preferably 0.5 to 10,000 ppm, in the resin composition for optical lenses to enable color correction of a lens together with addition of a UV absorbent, an optical resin and monomers.

The resin composition for optical lenses according to the present invention may further include a typical release agent and a typical polymerization initiator. The release agent may be selected from the group consisting of a fluorine-based non-ionic surfactant, a silicon-based non-ionic surfactant, an alkyl quaternary ammonium salt, and mixtures thereof. Preferably, the release agent is phosphoric acid ester. In addition, the polymerization initiator may be selected from among amine-based and tin-based compounds. These may be used alone or as a mixture thereof.

A polyurethane lens according to the present invention is evaluated as to properties of eyeglass lenses. For evaluation of the properties, (1) index of refraction ($n_D^{20}$) and Abbe's number (vd), (2) heat resistance (Tg), and (3) thermal analysis were evaluated by the following methods.

(1) Index of refraction ($n_D^{20}$) and Abbe's number (vd): The index of refraction and Abbe's number were measured at 20° C. using an ABBE refractometer (1T model of ATAGO Co., Ltd.).
(2) Heat resistance: Glass transition temperature (Tg) of a specimen was measured using a heat analyzer DSC N-650 (SCINCO Co., Ltd.) and defined as heat resistance.
(3) Thermal analysis: Thermal analysis of a lens was directly performed on a plastic lens sample using D1 (SINCO Co., Ltd.).

(Representative Method of Manufacturing Optical Lens)

Monomers constituting the polyisocyanate and monomers constituting the polythiol are mixed and stirred in a particular ratio. Then, predetermined amounts of a release agent, a UV absorbent, an organic dye, and a curing catalyst are added to the prepared mixture. Then, a prepared polyurethane optical resin composition is subjected to degassing for a predetermined period of time and injected into a glass mold assembled by an adhesive tape.

Thereafter, the glass mold containing the mixture is placed in a forcible circulation type oven. In the oven, the mixture is polymerized by maintaining the mixture at room temperature for a predetermined period, gradually elevating the temperature of the mixture, and maintaining the mixture at the elevated temperature, followed by cooling the mixture.

After completion of polymerization, a resulting product is separated from the mold, thereby providing a urethane optical lens. Then, the lens is subjected to annealing at 120° C. for 1 hour and 40 minutes. After annealing, a non-treated lens is released from the glass mold, thereby providing an optical lens having a thickness of 1.2 mm. The prepared optical lens is processed to a diameter of 80 mm and sequentially subjected to ultrasonic washing in an alkali aqueous washing liquid, annealing at 120° C. for 2 hours, and coating by dipping in a silicone-based hard liquid, followed by heat drying.

The optical lens according to the present invention may be subjected to physical and chemical treatments, such as surface grinding, antistatic treatment, hard coat treatment, non-reflection coat treatment, dyeing treatment, and photochromic treatment for the purpose of imparting antireflective properties, high hardness, abrasive resistance, chemical resistance, anti-fog properties, fashionability and the like, as needed.

Example

Hereinafter, the present invention will be described in more detail with preparative examples and examples. However, it should be understood that these preparative examples and examples are provided for illustration only and the present invention is not limited thereto.

A preparation starting material can be easily produced from propylene oxide. 1-mercaptopropan-2-ol was obtained from products of Aldrich GmbH and 2-mercaptopropan-1-ol was obtained from products of Bocsic Co., Ltd.

Preparative Examples 1 to 9 of Polyol

Preparative Example 1: 1-chloro-3-((2-hydroxypropyl)thio)propane-2-ol [Compound 1]

500 g (5.43 moles) of 1-mercaptopropan-2-ol (Aldrich Co., Ltd.) and 54.9 g of triethylamine were placed in a reactor. Then, with the temperature of the reactor set to 15°

C., 502 g (5.43 moles) of epichlorohydrin was slowly added dropwise to the solution, thereby preparing 1,002 g of Compound 1. According to NMR-data of FIG. 1, the compound has the following chemical properties: $^1$H-NMR (D$_2$O), δ ppm=1.26 (3H, d, CH$_3$), 2.66 to 2.90 (4H, m, CH$_2$—S), 3.70 to 3.82 (2H, m, CH$_2$—Cl).

Preparative Example 2: 2-((3-chloro-2-hydroxypropyl)thio)propane-1-ol [Compound 2]

500 g (5.43 moles) of 1-mercaptopropan-2-ol and 55.0 g of triethylamine were placed in a reactor. Then, with the temperature of the reactor set to 15° C., 502 g (5.43 moles) of epichlorohydrin was slowly added dropwise to the solution, thereby preparing 1,002 g of Compound 2. According to NMR-data, the compound has the following chemical properties: $^1$H-NMR (D2O), δ ppm=1.25 (3H, d, CH$_3$), 2.66 to 2.90 (4H, m, CH$_2$—S), 3.65 to 3.82 (2H, m, CH$_2$—Cl).

Preparative Example 3: 3-((2-hydroxypropyl)thio)propane-1,2-diol [Compound 3]

Figure 2:
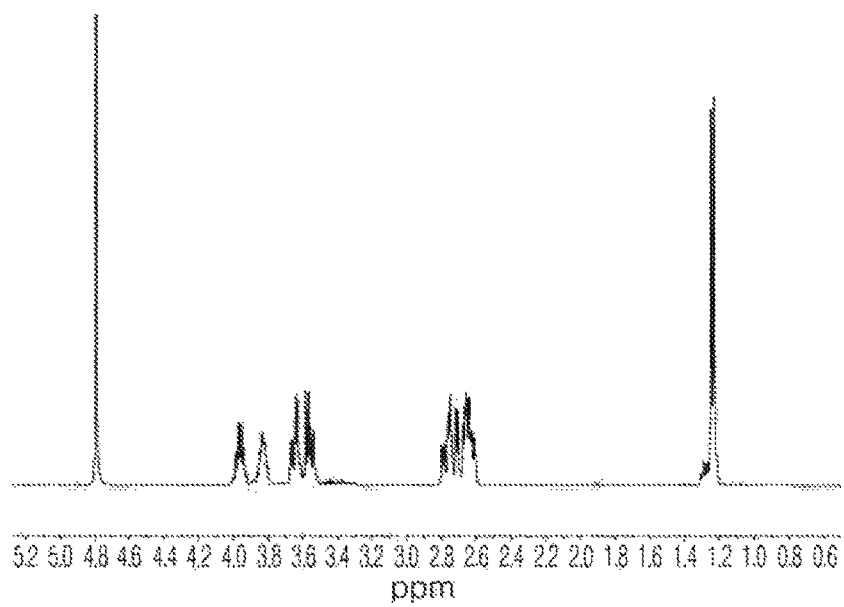
FIG. 2 shows $^1$H-NMR spectrum of Example 3 (Compound 3) according to the present invention.

After 200 g of H$_2$O was supplied to a reactor, 105 g (1.03 moles) of triethylamine was added thereto and the temperature of the reactor was set to 25° C. while stirring the mixture in the reactor. 200 g (2.17 moles) of 1-mercaptopropan-2-ol was added to the reactor, and, with the temperature of the reactor set to 20° C., 169 g (2.28 moles) of glycidol was added dropwise to the solution for about 1 hour and additionally stirred, thereby preparing 353.6 g of Compound 3. According to NMR-data of FIG. 2, the compound has the following chemical properties: $^1$H-NMR (D2O), δ ppm=1.22 (6H, d, CH$_3$), 2.63 to 2.81 (4H, m, CH$_2$—S), 3.47 to 4.1 (4H, m, CH—O, CH$_2$-0), 4.80 (3H, s, OH).

Preparative Example 4: 1,3-bis[(2-hydroxypropyl)thio]-2-propane-2-ol [Compound 4]

Figure 3:
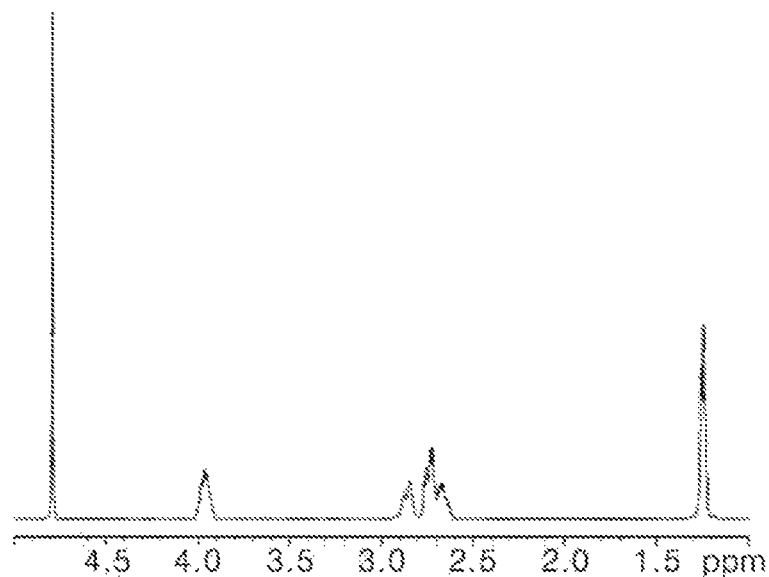
FIG. 3 shows $^1$H-NMR spectrum of Example 4 (Compound 4) according to the present invention.

After 87.5 g of H$_2$O was supplied to a reactor, 87.3 g (1.09 moles) of sodium hydroxide was added thereto and the temperature of the reactor was set to 25° C. while stirring the mixture in the reactor. 199.2 g (2.16 moles) of 1-mercaptopropan-2-ol was added to the reactor, which in turn was set to a temperature of 20° C. Thereafter, 100 g (1.08 mole) of epichlorohydrin was added dropwise to the reactor for about 1 hour, followed by stirring for 1 hour, thereby preparing 259.4 g of Compound 4. According to NMR-data of FIG. 3, the compound has the following chemical properties: $^1$H-NMR (D2O), δ ppm=1.24 (6H, d, CH$_3$), 2.63 to 2.87 (8H, m, CH$_2$—S), 3.97 (3H, m, CH—O), 4.80 (3H, s, OH).

Preparative Example 5: bis[3-((2-hydroxypropyl)thio)-2-hydroxypropyl]sulfide [Compound 5]

Figure 4:
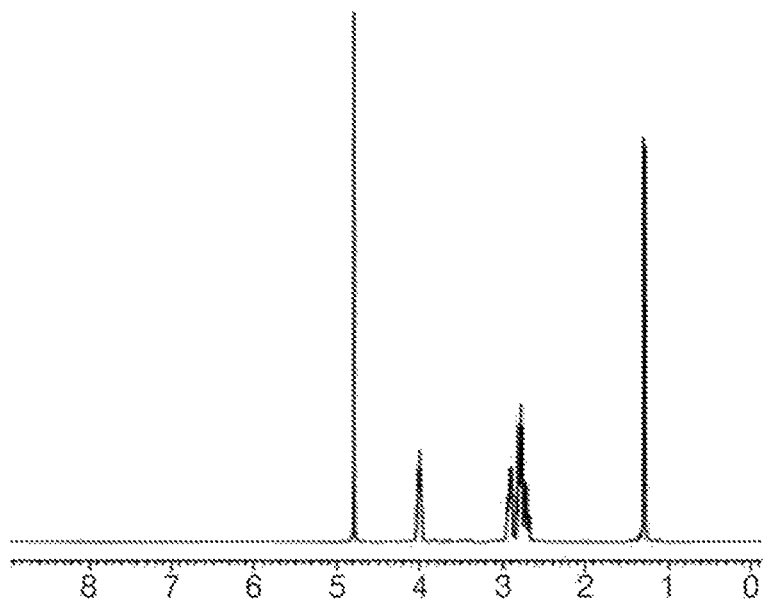
FIG. 4 shows $^1$H-NMR spectrum of Example 5 (Compound 5) according to the present invention.

With a reactor maintained at 40° C., 890 g (2.71 moles) of an aqueous sodium sulfate solution was slowly added dropwise to Compound 1 prepared in Preparative Example 1, followed by stirring for 1 hour, thereby preparing 896.6 g of Compound 5. According to NMR-data of FIG. 4, the compound has the following chemical properties: $^1$H-NMR (D$_2$O), δ ppm=1.29 (6H, d, CH$_3$), 2.67 to 2.95 (8H, m, CH$_2$—S), 4.02 (4H, m, CH—O)

Preparative Example 6: bis[3-((1-hydroxy-propane-2-yl)thio)-2-hydroxypropyl]sulfide [Compound 6]

With a reactor maintained at 40° C., 890 g (2.71 moles) of an aqueous sodium sulfate solution was slowly added dropwise to Compound 2 prepared in Preparative Example 2, followed by stirring for 1 hour, thereby preparing 892.3 g of Compound 6. According to NMR-data, the compound has the following chemical properties: $^1$H-NMR (D$_2$O), δ ppm=1.25 (6H, d, CH$_3$), 2.65 to 2.95 (8H, m, CH$_2$—S), 4.07 (4H, m, CH—O).

Preparative Example 7: 1-((3-chloro-2-hydroxypropyl)thio)botane-2ol [Compound 7]

Figure 5:
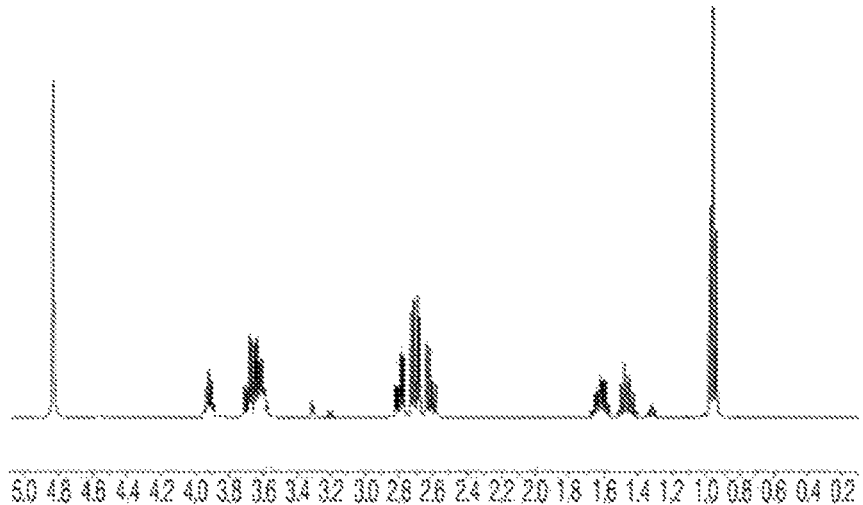
FIG. 5 shows $^1$H-NMR spectrum of Example 7 (Compound 7) according to the present invention.

500 g (4.71 moles) of 1-mercaptobutane-2-ol and 47.6 g of triethylamine were placed in a reactor. Then, with the temperature of the reactor set to 15° C., 435.7 g (4.71 moles) of epichlorohydrin was slowly added dropwise to the solution, thereby preparing 935.6 g of Compound 7. According to NMR-data of FIG. 5, the compound has the following chemical properties: $^1$H-NMR (MeOD), δ ppm=0.94 (3H, t, CH$_3$), 1.4 to 1.65 (2H, m, CH$_2$), 2.58 to 2.82 (4H, m, CH$_2$—S—CH$_2$), 3.58 to 3.92 (3H, m, CH—O/CH$_2$—Cl), 4.82 (2H, s, OH)

Preparative Example 8: bis[3-((2-hydroxybutyl)thio)-2-hydroxypropyl]sulfide[Compound 8]

Figure 6:
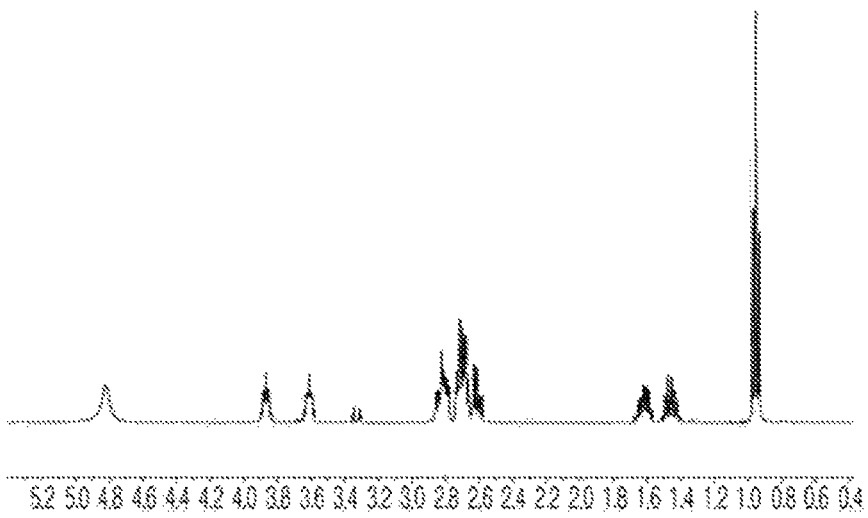
FIG. 6 shows $^1$H-NMR spectrum of Example 8 (Compound 8) according to the present invention.

With a reactor maintained at 40° C., 782 g (2.35 moles) of an aqueous sodium sulfate solution was slowly added dropwise to Compound 7 prepared in Preparative Example 7, followed by stirring for 1 hour, thereby preparing 844.2 g of Compound 8. According to NMR-data of FIG. 6, the compound has the following chemical properties.
$^1$H-NMR (MeOD), δ ppm=0.96 (6H, t, CH$_3$), 1.41 to 1.68 (4H, m, CH$_2$), 2.58 to 2.89 (12H, m, CH$_2$—S), 3.61 (2H, m, CH—O), 3.88 (2H, m, CH—O), 4.81 (4H, S, OH)

Preparative Example 9: 1,3-bis[(2-hydroxybutyl)thio]propane-2-ol[Compound 9]

Figure 7:
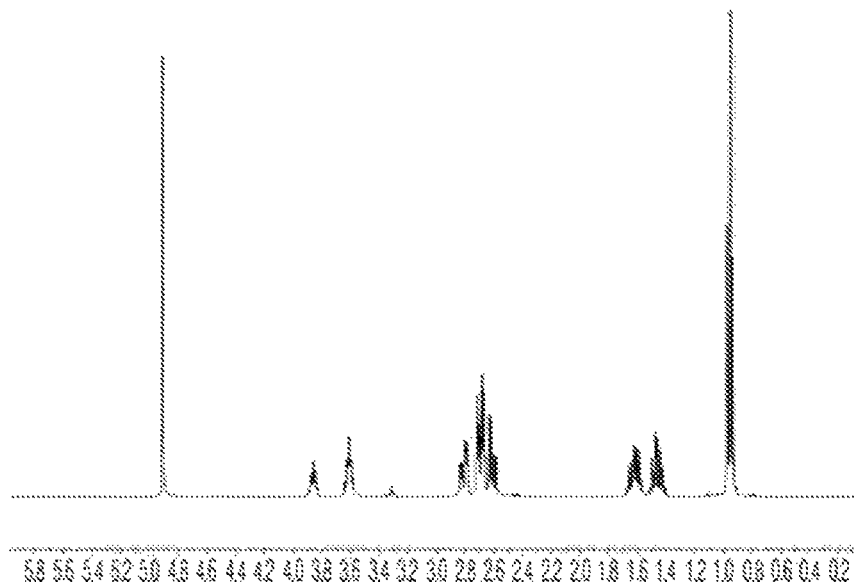
FIG. 7 shows $^1$H-NMR spectrum of Example 9 (Compound 9) according to the present invention.

After 87.5 g of H$_2$O was supplied to a reactor, 87.3 g (1.09 moles) of sodium hydroxide was added thereto and the temperature of the reactor was set to 25° C. while stirring the mixture in the reactor. 229.5 g (2.16 moles) of 1-mercaptobutane-2-ol was added to the reactor, which in turn was set to 20° C. Thereafter, 100 g (1.08 moles) of epichlorohydrin was added dropwise to the reactor for about 1 hour, followed by stirring for 1 hour, thereby preparing 290.1 g of Compound 9. According to NMR-data of FIG. 7, the compound has the following chemical properties:
$^1$H-NMR (MeOD), δ ppm=0.95 (6H, t, CH$_3$), 1.40 to 1.68 (4H, m, CH$_2$), 2.58 to 2.89 (12H, m, CH$_2$—S), 3.61 (2H, m, CH—O), 3.88 (2H, m, CH—O), 4.91 (3H, s, OH)

Examples 10 to 12 of Polythiol

Preparative Example 10: (Preparation of 2-((1-mercaptopropan-2-yl)thio)propane-1,3-dithiol) [Compounds 10-1 to 10-4] (GPT)

In a reactor, 904 g (8.68 moles) of 35% HCl aqueous solution was added to Compound 3 prepared in Preparative Example 3, followed by adding 512 g (6.72 moles) of thiourea. Then, the components were stirred at 110° C. for 12 to 24 hours under temperature elevation and reflux conditions. Thereafter, with the mixture cooled to room temperature, 600 mL of toluene was added to the mixture and 663.68 g (9.76 moles) of 25% aqueous ammonia was slowly added to the mixture, followed by hydrolysis at 65° C. for 3 hours. An organic layer obtained by the above process was cooled to room temperature, followed by sequentially washing with 200 mL of 36% hydrochloric acid solution, 200 mL of water, 200 mL of a diluted aqueous ammonia, and 200 mL of water three times. The organic layer was separated and subjected to vacuum evaporation, thereby preparing 300 g of a colorless and transparent polythiol compound.

Figure 8:
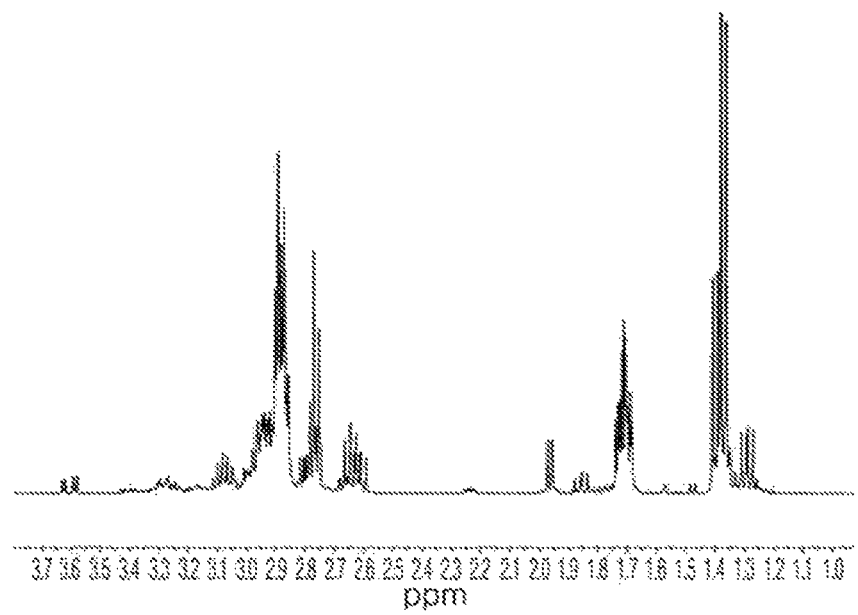
FIG. 8 shows $^1$H-NMR spectrum of Example 10 (a mixture of Compounds 10-1 to 10-4, GPT) according to the present invention.

As a result of analysis of the prepared compound under the same conditions as those of high performance liquid chromatography of Preparative Example 11, the prepared compound consisted of about 60% to about 70% of Compound 10-1 as a main reaction product and 40% or less of Compounds 10-2 to 10-4, which are isomers of Compound 10-1. Referring to FIG. 8 showing NMR-data of a mixture of Compounds 10-1 to 10-4, Compounds 10-1 to 10-4 have the following chemical properties: $^1$H-NMR (CDCl$_3$), δ ppm=1.25 to 1.42 (3H, m, CH$_3$), 1.68 to 2.0 (3H, m, SH), 2.59 to 3.33 (8H, m, CH$_2$—S, CH—S); Index of refraction ($n_D^{20}$): 1.618

Preparative Example 11: (Preparation of 3-((1-mercaptopropan-2-yl)thio)-2((1-mercaptopropan-2-yl)thio)propane-1-thiol) [Compounds 11-1 to 11-4] (MPT)

In a reactor, 394 g (3.78 moles) of 35% HCl aqueous solution was added (at 30° C. or less) to Compound 4 prepared in Preparative Example 4, followed by adding 250.9 g (3.30 moles) of thiourea. Then, the components were stirred at 110° C. for 12 to 24 hours under temperature elevation and reflux conditions. Then, with the mixture cooled to room temperature, 550 mL of toluene was added to the mixture and 282.7 g (4.32 moles) of 25% aqueous ammonia was slowly added to the mixture, followed by hydrolysis at 65° C. for 3 hours. The temperature of an organic layer obtained by the above process was cooled to room temperature, followed by sequentially washing with 57 mL of 36% hydrochloric acid solution and 400 mL of water. The organic layer was separated and subjected to vacuum evaporation, thereby preparing 290 g of a colorless and transparent polythiol compound.

Figure 9:
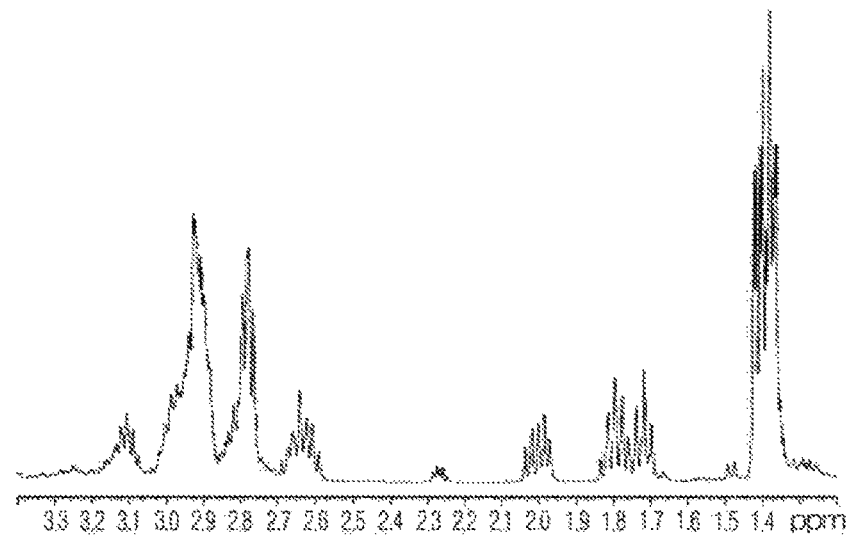
FIG. 9 shows $^1$H-NMR spectrum of Example 11 (a mixture of Compounds 11-1 to 11-4, MPT) according to the present invention.

The compound prepared in Preparative Example 11 also has four isomers. Thus, as a result of analysis of the prepared compound under the same conditions as those of high performance liquid chromatography described below, Compound 11-1 (main reaction product) was present in an amount of about 84% to about 88% and each of Compounds 11-2 to 11-4, which are isomers of Compound 11-1, was present in an amount of 8% or less. According to NMR-data FIG. 9, Compounds 11-1 to 11-4 have the following chemical properties: $^1$H-NMR (CDCl$_3$), δ ppm=1.35 to 1.42 (6H, m, CH$_3$), 1.70 to 2.28 (3H, m, SH), 2.59 to 3.16 (11H, m, CH$_2$—S, CH—S); CH—S); Index of refraction ($n_D^{20}$): 1.601

The Conditions for High Performance Liquid Chromatography (HLPC) for Confirmation of Isomers were as Follows:
Conditions for High Performance Liquid Chromatography (HLPC)
  Column: Wathers ODS (Φ 6 mm×250 mm)
  Moving phase: acetonitrile/10 mmol—Aqueous sodium acetate solution
  90/10 (vol/vol)→0/100 (vol/vol) (change for 20 minutes)
  Column temperature: 25° C.
  Flux: 1.0 ml/min
  Detector: UV detector, wavelength: 215 nm
  Measurement solution concentration: 100 mg of a specimen in 10 ml acetonitrile
  Injection amount: 10 μL
  Peak area ratio of isomer A ratio of an integrated area of each isomer to the sum of total areas of Compound 11-1 produced as the main reaction product of the polythiol compound and Compounds 11-2, 11-3 and 11-4 produced as isomers thereof was calculated. As a result, Compound 11-2 was present in a ratio of 0.03 to 0.04, Compound 11-3 was present in a ratio of 0.04 to 0.05, and Compound 11-4 was present in a ratio of 0.03 to 0.08.

Preparative Example 12: 3,3'-thiobis(2-((1-mercaptopropan-2-yl)thio)-1-propanethiol) [Compounds 12-1 to 12-10] (BPT)

In a reactor, 2,239.6 g (13.5 moles) of 49% hydrobromic acid and 836.3 g (10.9 moles) of thiourea were added to Compound 5 prepared in Preparative Example 5, followed by heating at 105° C. for 6 hours while stirring the mixture. Then, the mixture was cooled to room temperature, and 2,000 g of toluene and 1,700 g of water were added to the mixture, which in turn was slowly heated to 70° C. Then, 1,596 g (9 moles) of 25% aqueous ammonia was slowly added dropwise to the mixture. A water layer was removed from the mixture and an organic layer was cooled to room temperature and washed with 100 g of 36% hydrochloric acid and 1,000 g of distilled water, followed by vacuum distillation, thereby preparing 1,070 g of Compounds 12-1 to 12-10.

Figure 10:
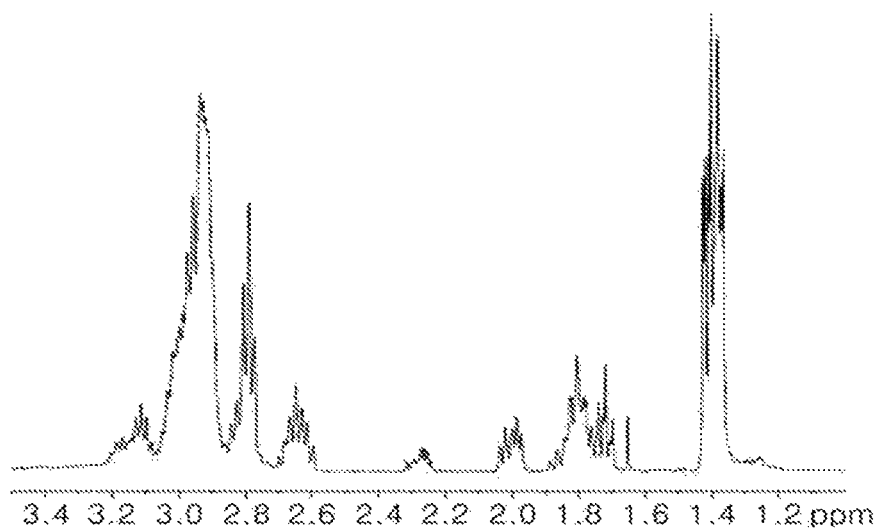
FIG. 10 shows $^1$H-NMR spectrum of Example 12 (a mixture of Compounds 12-1 to 12-10, BPT) according to the present invention.

As a result of analysis of the prepared compounds under the same conditions as those of high performance liquid chromatography of Preparative Example 11, Compound 12-1 was present as a main reaction product in an amount of about 63% to about 70% and each of Compounds 12-2 and 12-3, which are isomers of Compound 12-1, was present in an amount of 14% or less. Other isomers were present in a total amount of about 2% to about 8%. Referring to FIG. 10 showing NMR-data of a mixture of Compounds 12-1 to 12-10, Compound 12-1 has the following chemical properties:
1H-NMR (CDCl$_3$), δ ppm=1.36 to 1.4 (6H, m, CH$_3$), 1.65 to 2.32 (4H, m, SH), 2.6 to 3.18 (16H, m, CH$_2$—S, CH—S); index of refraction ($n_D^{20}$): 1.621

Preparative Example 13: 2,2'-((thiobis(1-mercaptopropan-3,2-diyl))bis(sulfondiyl))bis(butane-1-thiol) [Compounds 13-1 to 13-10] (BBT)

In a reactor, 1,225.2 g (11.8 moles) of 35% HCl aqueous solution was added (at 30° C. or less) to Compound 8 prepared in Preparative Example 8, followed by adding 727.6 g (9.56 moles) of thiourea. Then, the components were stirred at 110° C. for 12 to 24 hours under temperature elevation and reflux conditions. Thereafter, with the mixture cooled to room temperature, 2,000 mL of toluene was added to the mixture and 846.6 g (12.95 moles) of 25% aqueous ammonia was slowly added to the mixture, followed by hydrolysis at 65° C. for 3 hours. An organic layer obtained by the above process was cooled to room temperature, followed by sequentially washing with 1000 mL of 36% hydrochloric acid solution and 100 mL of water. The organic layer was separated and subjected to vacuum evaporation, thereby preparing 1,104 g of a colorless and transparent polythiol compound as Compound 15.

Figure 11:
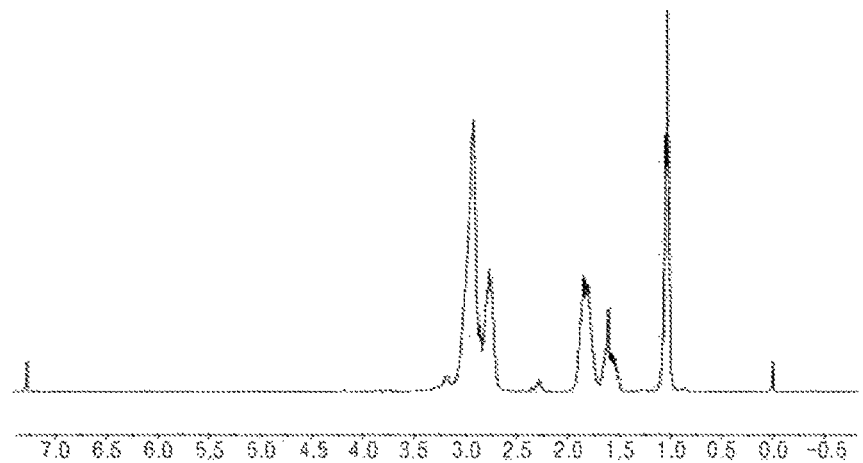
FIG. 11 shows $^1$H-NMR spectrum of Example 13 (a mixture of Compounds 13-1 to 13-10, BBT) according to the present invention.

As a result of analysis of the prepared compound under the same conditions as those of high performance liquid chromatography of Preparative Example 11, Compound 13-1 was present as a main reaction product in an amount of about 60% to about 70% and each of Compounds 13-2 and 13-3, which are isomers of Compound 13-1, was present in an amount of 15% or less. Other isomers were present in a total amount of about 2% to about 3%. According to NMR-data of FIG. 11, the compound has the following chemical properties.

1H-NMR (CDCl$_3$), δ ppm=1.11 (6H, m, CH$_3$), 1.65 (4H, m, SH), 1.75 to 1.91 (4H, m, CH$_2$), 2.62 to 3.15 (16H, m, CH—S/CH$_2$—S); index of refraction (n$_D^{20}$): 1.602

Preparative Example 14: 3-((1-mercaptobutane-2-yl)thio)-2-((1-mercaptobutane-2-yl)thio)propane-1-thiol[Compounds 14-1 to 14-4] ((MBT)

In a reactor, 394 g (3.78 moles) of 35% HCl aqueous solution was added (at 30° C. or less) to Compound 9 prepared in Preparative Example 9, followed by adding 250.9 g (3.30 moles) of thiourea. Then, the components were stirred at 110° C. for 12 to 24 hours under temperature elevation and reflux conditions. Thereafter, with the mixture cooled to room temperature, 550 mL of toluene was added to the mixture and 282.7 g (4.32 moles) of 25% aqueous ammonia was slowly added to the mixture, followed by hydrolysis at 65° C. for 3 hours. An organic layer obtained by the above process was cooled to room temperature, followed by sequentially washing with 57 mL of 36% hydrochloric acid solution and 400 mL of water. The organic layer was separated and subjected to vacuum evaporation, thereby preparing 318.2 g of colorless and transparent polythiol compounds as Compounds 14-1 to 14-4.

Figure 12:
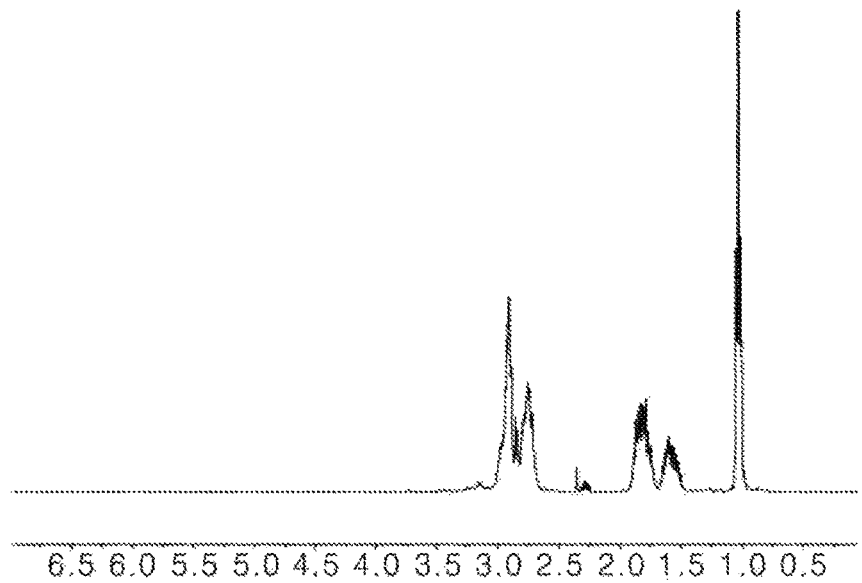
FIG. 12 shows $^1$H-NMR spectrum of Example 14 (a mixture of Compounds 14-1 to 14-4, MBT) according to the present invention.

As a result of analysis of the prepared compounds under the same conditions as those of high performance liquid chromatography of Preparative Example 11, Compound 14-1 was present as a main reaction product in an amount of about 80% to about 95% and each of Compounds 14-2 to 14-4, which are isomers of Compound 14-1, was present in an amount of 5% or less. According to NMR-data of FIG. 12, the compound has the following chemical properties.

1H-NMR (CDCl$_3$), δ ppm=1.11 (6H, t, CH$_3$), 1.62 (3H, m, SH), 1.75 to 1.89 (4H, m, CH$_2$), 2.62 to 3.0 (9H, m, CH—S/CH$_2$—S); Index of refraction (n$_D^{20}$): 1.599

As described above, the compound according to the present invention is composed of a mixture of a polythiol main product containing a primary thiol having a mercaptomethyl group and polythiol isomers containing a secondary thiol. Thus, according to the present invention, it can be understood that the polythiol compound of Compound 10 (GPT) theoretically consists of a main compound and 4 isomers, and the polythiol compound of each of Compound 11 (MPT) and Compound 14 (MBT) theoretically consists of a main compound and 4 isomers excluding isomers having the same atom arrangement among 10 isomers thereof. On the other hand, the polythiol compound of each of Compound 12 (BPT) and Compound 13 (BBT) has 10 isomers excluding isomers having the same atom arrangement among 16 isomers thereof.

On the other hand, as mentioned in Background Art, Patent Document 4 discloses substitution of an isothiouronium salt at a carbon location having a hydroxyl group in preparation of an isothiouronium salt compound through reaction of a sulfur-containing polyol with thiourea under acid conditions. However, it is believed that rearrangement allowing selective introduction of thiourea through steric hindrance also occurs in an activation process in which an episulfonium salt having a sulfur atom is generated. Then, the isothiouronium salt compound having a modified main chain structure is hydrolyzed, thereby producing a compound in which a mercaptomethyl group is introduced into a main chain structure of a polythiol compound.

In summary, in the process of preparing the polythiol compound according to the present invention, it is not believed that only the compound having an isothiouronium salt substituted at the carbon location having a hydroxyl group is generated without rearrangement through steric hindrance, as disclosed in Patent Document 4. Therefore, it is believed that a secondary thiol compound having a thiol group at a carbon location where a hydroxyl group of a polyol intermediate compound is placed cannot be prepared as a main reaction product in Preparative Example (1) of the prior patent document.

Next, optical lenses were manufactured using the polythiol compounds according to the present invention together with a polyisocyanate typically used in the art and compared with optical lenses of Comparative Examples 1 to 4. In particular, the lenses were prepared to evaluate properties of lenses according to each polythiol in Lens Preparation Examples 1 to 13.

1) According to the representative method of manufacturing an optical lens described above, each of the polythiol compounds prepared in Preparative Examples, a polyisocyanate compound, and additives (release agent and polymerization initiator) were mixed in amounts as listed in Tables 1 to 4 and formed into an optical lens through polymerization in a mold, followed by evaluation of index of refraction, Abbe's number, heat resistance, and the like.

Here, the release agent was a Zelec UN (Dupont). The polymerization initiator was selected from among dibutyltin dichloride and tin compounds. In addition, UV absorbents, bluing agents (organic dyes, organic pigments, inorganic pigments, and the like), and the like were used, as needed. In the following examples, the content of each component is represented in terms of wt % with reference to gram (g).

2) Multilayer splitting was observed by leaving prepared lenses under conditions of 75% RH (relative humidity) and an inner temperature of 80° C. for 1 hour. Splitting was evaluated by the following standards, that is, A: no splitting, B: 1 or more split marks, and C: significant splitting.

3) For evaluation of dyeing properties, each of plastic lenses prepared using compositions, for example, XDI/BPT, XDI/BET, XDI/MPT, XDI/GST, and the like, listed in each table, was dipped in a dyeing bath filled with a mixture of 500 g of distilled water and 17.5 g of ONS black at a temperature of 85° C. to 95° C. for 5 minutes. Then, the degree of dyeing of each lens was evaluated.

4) In Examples 1 to 13 and Tables 1 to 4, BPT, MPT, GPT, BBT and MBT refer to the compounds prepared in Preparative Examples 10, 11, 12, 14 and 15, respectively, and acronyms of these compounds are shown in the aforementioned tables. In addition, isocyanate compounds such as XDI, Biuret, HDI, NBDI, IPDI, and HMDI used together with well-known polythiol compounds such as GST and BET (3,3'-thiobis[2-[(2-mercaptoethyl)thio]-1-propanethiol) are also mentioned above and thus detailed description thereof will be omitted.

In Lens Preparation Examples 1 and 2, lenses were prepared using XDI as an isocyanate and MPT and BPT as the polythiol compounds according to the present invention, instead of GST and BET, respectively. Then, the prepared lenses were compared with commercially available lenses of Comparative Examples 1 and 2.

In Lens Preparation Examples 3 and 4, lenses were prepared using a Biuret compound as an isocyanate, and MPT and BPT instead of GST and BET, respectively. Then, the prepared lenses were compared with commercially available lenses of Comparative Examples 3 and 4. In Lens Preparation Examples 5 to 10, lenses were prepared using various isocyanates (NBDI, IPDI, and HIMIDI) instead of XDI. Table 3 shows improvement of functionality such as heat resistance and dyeing properties due to increase in glass transition temperature Tg. In addition, lenses were prepared using XDI and novel polythiol compounds, such as GPT, MBT, and BBT, as the polythiol compound according to the present invention. Table 4 shows the index of refraction, Abbe's number, heat resistance, dyeing properties and functionality of these lenses.

Lens Preparation Examples 1 and 2

The following table shows the index of refraction, Abbe's number, heat resistance, and multilayer splitting of each of the lenses according to the present invention and the lenses of comparative examples.

like. On the other hand, this lens has good dyeing properties in order to improve functionality, such as UV or sunlight shielding. In order to solve the problem of low heat resistance, Mitsui Chemical Co., Ltd. developed a novel product (Comparative Example 2). A lens of Comparative Example 2 is mainly composed of XDI and BET instead of GST as a polythiol compound. However, it is known in the art that this lens fails to satisfy dyeing properties for improvement in functionality, despite improvement in heat resistance.

In Table 1, the lens of Comparative Example 1 suffering from splitting of the multilayer coating is compared with the lenses of Examples 1-1 to 1-3 according to the present invention. Referring to Table 1, the lenses of the examples had similar indices of refraction to the lens of Comparative Example 1 and 12.3° C. higher heat resistance than the lens of Comparative Example 1, and improved Abbe's number, particularly dyeing properties. Upon multilayer coating after manufacture of the lens, the lens of Comparative Example 1 suffered from damage to the multilayer coating under conditions of 75% RH and 80° C., whereas the lens of Example 1 maintained an original shape thereof without suffering from damage to the multilayer coating under the same conditions. Therefore, it could be confirmed that MPT

TABLE 1

|  |  | Ex. 1-1 | Ex. 1-2 | Ex. 1-3 | Ex. 2-1 | Ex. 2-2 | Ex. 2-3 | Comp. Ex. 1 | Comp. Ex. 2 |
|---|---|---|---|---|---|---|---|---|---|
| Monomers (g) | XDI | 10 | 10 | 10 | 9.76 | 9.76 | 9.76 | 11 | 11 |
|  | MPT | 10.2 | 10.2 | 10.2 |  |  |  |  |  |
|  | BPT |  |  |  | 10.91 | 10.91 | 10.91 |  |  |
|  | GST |  |  |  |  |  |  | 9.595 |  |
|  | BET |  |  |  |  |  |  |  | 9.87 |
| Release agent |  | 0.024 | 0.024 | 0.024 | 0.024 | 0.024 | 0.024 | 0.024 | 0.024 |
| Polymerization initiator |  | 0.004 | 0.004 | 0.004 | 0.004 | 0.004 | 0.004 | 0.004 | 0.004 |
| Lens properties | $n_D^{20}$ | 1.641 | 1.641 | 1.640 | 1.650 | 1.650 | 1.650 | 1.657 | 1.655 |
|  | Abbe's number | 33.2 | 33.5 | 33.3 | 32.3 | 32.5 | 32.4 | 31 | 31 |
|  | Heat resistance (° C.) | 97.3 | 96.0 | 97.6 | 103.5 | 103.0 | 103.1 | 85.0 | 100.0 |
|  | Dyeing property | ⊚ | ⊚ | ⊚ | ○ | ○ | ○ | ○ | ○ |
|  | Multilayer splitting | A | A | A | A | A | A | B | A |

1) Comparative Example 1: A commercially available product of Mitsui Chemical Co., Ltd., index of refraction($n_D^{20}$): 1.657, and heat resistance: 85° C.
2) Comparative Example 2: A commercially available product of Mitsui Chemical Co., Ltd., index of refraction($n_D^{20}$): 1.655, and heat resistance: 100° C.
3) Dyeing properties: ⊚: Excellent, O: Good, Δ: Normal, X: Poor
4) Splitting: A: no splitting, B: one or more splitting marks; C: significant splitting 1) Comparative Example 1: A commercially available product of Mitsui Chemical Co., Ltd., index of refraction ($n_D^{20}$): 1.657, and heat resistance: 85° C.
2) Comparative Example 2: A commercially available product of Mitsui Chemical Co., Ltd., index of refraction ($n_D^{20}$): 1.655, and heat resistance: 100° C.
3) Dyeing properties: ⊚: Excellent, •: Good, Δ: Normal, X: Poor
4) Splitting: A: no splitting, B: one or more splitting marks; C: significant splitting The lens of Comparative Example 1 is mainly composed of XDI as an isocyanate and GST as a polythiol compound, and has a glass transition temperature Tg of about 85° C. and a disadvantage of low heat resistance. It is known in the art that this lens suffers from splitting of multilayer coating in a high temperature condition, such as a sauna bath and the corresponding to the polythiol compound according to the present invention had better properties than GST used in the art.

In addition, the lenses of Examples 2-1 to 2-3 had slightly better refractivity and heat resistance than the lens of Comparative Example 2 and exhibited good dyeing properties. Therefore, it could be confirmed that BPT corresponding to the polythiol compound according to the present invention had similar or better properties to or than BET used in the art.

Lens Preparation Examples 3 and 4

Lenses were prepared by the same method as the above examples except that hexamethylene diisocyanate biuret was used as an isocyanate instead of XDI and the amounts of components for compounds were changed as listed in Table 1.

TABLE 2

|  |  | Example 3 | Example 4 | Comparative Example 3 | Comparative Example 4 |
|---|---|---|---|---|---|
| Monomers (g) | Biuret | 13 | 12.88 | 13.46 | 15 |
|  | MPT | 6.99 |  |  |  |
|  | BPT |  | 7.11 |  |  |
|  | GST |  |  | 6.54 |  |
|  | BET |  |  |  | 8.61 |
| Release agent |  | 0.024 | 0.024 | 0.024 | 0.024 |
| Polymerization initiator |  | 0.0125 | 0.0125 | 0.0125 | 0.0125 |

TABLE 2-continued

|  |  | Example 3 | Example 4 | Comparative Example 3 | Comparative Example 4 |
|---|---|---|---|---|---|
| Lens properties | $n_D^{20}$ | 1.577 | 1.579 | 1.596 | 1.589 |
|  | Abbe's number | 40.1 | 34.8 | 39.3 | 35.8 |
|  | Heat resistance (° C.) | 84.7 | 96.7 | 75.8 | 86.6 |
|  | Dyeing property | ◉ | ◉ | ◉ | ◉ |
|  | Multilayer splitting | B | A | C | B |

In Table 2, the lenses of Examples 3 and 4 were prepared using the same isocyanate, that is, Biuret, as the lenses of Comparative Examples 3 and 4. As compared with the lens of Comparative Example 1, the lens of Example 3 improved in heat resistance by about 10° C. or more and exhibited very good dyeing properties, despite a lower index of refraction. Upon multilayer coating after manufacture of the lens, the lens of Comparative Example 3 suffered from damage to the multilayer coating under conditions of 75% RH and 80° C. However, the lens of Example 3 maintained an original shape thereof without suffering from damage to the multilayer coating under the same conditions. Therefore, it could be confirmed that MPT corresponding to the polythiol compound according to the present invention had better properties than GST used in the art.

As compared with the lens of Comparative Example 4, the lens of Example 4 improved in heat resistance by about 10° C. or more and exhibited very good dyeing properties (since the lens of Example 4 had good dyeing properties, both lenses had similar dyeing properties), despite a lower index of refraction. Therefore, it could be confirmed that BPT corresponding to the polythiol compound according to the present invention had similar or better properties to or than BET used in the art.

Lens Preparation Examples 5 to 10

Lenses were prepared by the same method as the above examples except that NBDI was used as an isocyanate and the amounts of components for compounds were changed as listed in Table 1.

TABLE 3

|  |  | Example 5 | Example 6 | Example 7 | Example 8 | Example 9 | Example 10 |
|---|---|---|---|---|---|---|---|
| Monomers (g) | NBDI | 10.34 | 10.21 |  |  |  |  |
|  | IPDI |  |  | 11 | 10.59 |  |  |
|  | HMDI |  |  |  |  | 12 | 11.41 |
|  | MPT | 9.65 |  | 9.52 |  | 8.79 |  |
|  | BPT |  | 10.4 |  | 10.41 |  | 8.58 |
| Release agent |  | 0.024 | 0.024 | 0.024 | 0.024 | 0.024 | 0.024 |
| Polymerization initiator |  | 0.0125 | 0.0125 | 0.0125 | 0.0125 | 0.0125 | 0.0125 |
| Lens properties | $n_D^{20}$ | 1.604 | 1.614 | 1.581 | 1.589 | 1.583 | 1.590 |
|  | Abbe's number | 37.7 | 43 | 41.3 | 35.9 | 45.3 | 38.6 |
|  | Heat resistance (° C.) | 124.7 | 133.3 | 106.1 | 123.1 | 99.0 | 111.6 |
|  | Dyeing property | ○ | ○ | ○ | ○ | ◉ | ○ |
|  | Multilayer splitting | A | A | A | A | A | A |

Table 3 shows the contents of NBDI, IPDI, and HMDI among non-yellowing isocyanates applicable to transparent optical lenses. Here, the properties of lenses prepared by the same method as in the above examples were compared according to MPT and BPT. As an isocyanate compound used in preparation of lenses of Examples 5 and 6, NBDI provided an index of refraction of about 1.604 to 1.614 and a combination of NBDI-BPT provided a very high Abbe's number of about 43. The combination of NBDI-BPT provided a very high heat resistance of 133.3° C. and a combination of NBDI-MPT also provided a very high heat resistance of 124.7° C. and thus could be suitably used for improvement in heat resistance. These lenses also exhibited good properties in terms of dyeing properties and suppression of multilayer splitting.

Lenses of Examples 7 and 8 were prepared using IPDI. The lens of Example 7 prepared using a combination of IPDI-MPT had a heat resistance of about 106.1° C. and exhibited good dyeing properties, which are related to heat resistance. The lens of Example 8 had a heat resistance of about 123.1° C. and thus achieved significant improvement in heat resistance.

Lenses of Examples 9 and 10 were prepared using HMDI. The lens of Example 9 prepared using a combination of HMDI-MPT had a very high Abbe's number of about 45 and very good dyeing properties.

Lens Preparation Examples 11 to 13

The properties of lenses prepared using various isocyanates were evaluated in order to determined usability of the lenses as transparent lenses. Here, the lenses were evaluated as to the index of refraction, Abbe's number, heat resistance, dyeing properties, and the like. In addition, the lenses were prepared using XDI as an isocyanate and GPT, MBT or BBT having an elongated chain structure, such as butylene oxide, as the polythiol instead of MPT or BPT, which are derivatives of propylene oxide, to determine applicability of GPT, MBT and BBT together with XDI.

TABLE 4

|  |  | Example 11 | Example 12 | Example 13 |
|---|---|---|---|---|
| Monomers (g) | XDI | 11.36 | 10.405 | 10.13 |
|  | GPT | 10.03 |  |  |
|  | MBT |  | 13.5 |  |
|  | BBT |  |  | 13.24 |
|  | Release agent | 0.024 | 0.024 | 0.024 |
|  | Polymerization initiator | 0.004 | 0.004 | 0.004 |
| Lens properties | $n_D^{20}$ | 1.649 | 1.632 | 1.638 |
|  | Abbe's number | 27.5 | 30 | 32.5 |
|  | Heat resistance (° C.) | 110.07 | 78.5 | 94.2 |
|  | Dyeing property | ○ | ◎ | ◎ |
|  | Multilayer splitting | A | C | A |

In Table 4, the lenses of Examples 11, 12, and 13 had an index of refraction of 1.63 or more, despite lower indices of refraction than those of the lenses of Comparative Examples 1 and 2 shown in Table 1, thereby showing that the compound according to the present invention can be applied to materials requiring relatively high refractivity and ultrahigh refractivity. In addition, the lenses prepared in these examples exhibited improvement in heat resistance, dyeing properties, and suppression of multilayer splitting.

For the lens of Example 11, such differences in effect resulted from the use of GPT, which is a polythiol prepared using a polyol of Compound 3 prepared using 1-mercapto-propan-2-ol derived from propylene oxide and glydicol instead of epichlorohydrin, instead of GST used in preparation of the lens of Comparative Example 1 in Table 1. According to the present invention, when the volume of the polythiol increases through substitution of a methyl group or an ethyl group to a side chain of the polythiol, the glass transition temperature of the lens is maintained at 110° C., thereby improving heat resistance while providing good dyeing properties for improvement in functionality.

The lenses of Examples 12 and 13 were prepared using a polyol and a polythiol, which were prepared from butylene oxide instead of propylene oxide. The lens of Example 12 prepared using MBT instead of GST exhibited a high index of refraction and good dyeing properties, despite an unexpectedly low glass transition temperature Tg. The lens of Example 13 prepared using BBT instead of BET had a high index of refraction of 1.638 and a glass transition temperature Tg of 94.2° C., providing suitable heat resistance for coloration. From these results, it could be seen that the polyol and the polythiol compounds according to the present invention have applicability to novel polythiol or urethane optical materials.

The properties of the optical lenses of Examples 1 to 13 prepared using various polythiol compounds according to the present invention were compared with the properties of the lenses of Comparative Examples 1 to 4. As a result, it could be seen that the lenses according to the present invention generally had improved heat resistance to suppress multilayer splitting in a high temperature condition, such as a sauna bath and the like. In addition, it could be seen that the lenses according to the present invention were changed to exhibit the most suitable heat resistance through a magnification method. Further, it could be seen that the lenses according to the present invention had improvement in dyeing properties and Abbe's number to reduce fatigue on the eye even when a user wears the lens for a long period of time. Accordingly, it can be seen that a lens having improvement in heat resistance, dyeing properties, Abbe's number and suppressing multilayer splitting as compared with a lens in the art can be manufactured using the novel polythiol according to the present invention.

As a result, when the polythiol compound according to the present invention is used as a main component of a polymerizable composition for urethane-based optical materials, it is possible to manufacture an optical lens having good heat resistance. In particular, a conventional polythiol compound starts from '2-mercapto ethanol', whereas the polythiol compound according to the present invention starts from '2-mercaptopropanol', '1-mercaptopropan-2-ol', or '1-mercaptobutane-2-ol'. Thus, it is believed that the polythiol compound according to the present invention enables preparation of inexpensive urethane-based resins for optical materials and thus can be broadly applied to materials for optical lenses.

As a starting material of a conventional polythiol compound, 2-mercapto ethanol is prepared from ethylene oxide and hydrogen sulfide, whereas 1-mercaptopropan-2-ol of the polythiol compound according to the present invention may be prepared from propylene oxide and hydrogen sulfide. Ethylene oxide used in the art has a gaseous phase at room temperature and has problems of difficulty in handling and high possibility of explosion at room temperature, whereas propylene oxide used in the present invention has a liquid phase at room temperature and allows easy handling and good stability at room temperature. Accordingly, it is believed that the polythiol compound according to the present invention enables economically inexpensive preparation of 1-mercaptopropan-2-ol and thus has better economic feasibility than the conventional polythiol compound.

A polyurethane resin for optical materials according to the present invention is not limited to lenses. For example, it is possible to impart a polarizing function (a function of minimizing reflection on a surface of a non-metallic material allowing transmission of light only at a certain angle) and a dimming function (a function of enabling automatic control of illumination intensity based on surrounding environments and space usage) to a polyurethane resin substrate. Furthermore, it is possible to impart an eyesight correction function to the polyurethane resin substrate for eyeglass lenses.

On the other hand, the polyurethane resin substrate is applied to an eyeglass lens as an optical body in the above description. However, it should be understood that the optical body according to the present invention may also be applied as a construction material to large-area windows, such as sliding windows, single or double hung windows, side-hinged windows, and the like, which are used in buildings and the like, as needed. In order to apply the polyurethane resin composition according to the present invention to such large-area windows, the polyurethane resin composition may further include additives corresponding to additional functions. For example, the resin composition may be formed in a shape corresponding to a window frame, cured in a glass mold having various shapes, and released from the mold to be used in a building.

The invention claimed is:

1. A polythiol compound or an isomer thereof represented by Formula (b):

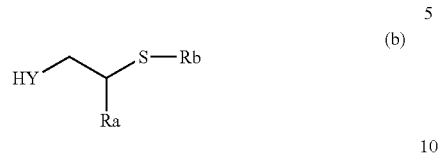

(wherein, Y is a sulfur atom; Ra is methyl or ethyl; and Rb is —CH(CH₂SH)CH₂SCH₂CH(CH₂SH)SCH(CH₃)CH₂SH).

2. The polythiol compound or an isomer thereof according to claim 1, wherein Ra is methyl.

3. A polymerizable poly(thio)urethane resin composition for an optical material comprising:
   (i) the polythiol compound or an isomer thereof according to claim 1 and (ii) a polyisocyanate.

4. The polymerizable poly(thio)urethane resin composition according to claim 3,
   wherein a mole ratio (NCO/SH) of a functional group (—NCO) of the polyisocyanate to a functional group (—SH) of the polythiol compound is in the range of 0.8 to 1.3.

5. A poly(thio)urethane resin being a cured product of the polymerizable poly(thio)urethane composition according to claim 3.

6. An optical lens comprising: the poly(thio)urethane resin according to claim 5.

* * * * *